(12) United States Patent
Lo et al.

(10) Patent No.: US 10,890,546 B2
(45) Date of Patent: Jan. 12, 2021

(54) TRANSIENT INDUCED MOLECULAR ELECTRONIC SPECTROSCOPY METHOD FOR STUDY OF MOLECULE INTERACTIONS

(71) Applicant: The Regents of the University of California, Oakland, CA (US)

(72) Inventors: Yu-Hwa Lo, San Diego, CA (US);
Tiantian Zhang, San Diego, CA (US);
Ti-Hsuan Ku, La Jolla, CA (US);
Yuanyuan Han, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/083,424

(22) PCT Filed: Mar. 9, 2017

(86) PCT No.: PCT/US2017/021486
§ 371 (c)(1),
(2) Date: Sep. 7, 2018

(87) PCT Pub. No.: WO2017/156210
PCT Pub. Date: Sep. 14, 2017

(65) Prior Publication Data
US 2019/0094166 A1     Mar. 28, 2019

Related U.S. Application Data

(60) Provisional application No. 62/305,766, filed on Mar. 9, 2016.

(51) Int. Cl.
*G01N 27/00* (2006.01)
*B01L 3/00* (2006.01)
(Continued)

(52) U.S. Cl.
CPC ........ *G01N 27/007* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

2002/0155476 A1* 10/2002 Pourmand ............ C12Q 1/6834
435/6.12
2005/0208647 A1* 9/2005 Holm-Kennedy ..........................
G01N 27/3276
435/287.2

(Continued)

FOREIGN PATENT DOCUMENTS

| EP | 1371974 A1 | 12/2003 |
|---|---|---|
| EP | 2950096 A2 | 12/2015 |

OTHER PUBLICATIONS

Demello, A.J., Control and detection of chemical reactions in microfluidic systems, Nature 442, 394-402 (2006).
(Continued)

*Primary Examiner* — Melanie Brown
(74) *Attorney, Agent, or Firm* — Perkins Coie LLP

(57) ABSTRACT

Methods, systems, and devices are disclosed for studying physical or chemical properties of molecules, and/or interactions between molecules such as protein-ligand interactions. The methods, systems, and devices involve transient induced molecular electronic spectroscopy (TIMES). In some configuration, a microfluidic channel having at least one inlet and at least one outlet is used for holding molecules for analyzing the molecules or interactions between molecules.

9 Claims, 12 Drawing Sheets

(51) Int. Cl.
G01N 27/02 (2006.01)
G01N 33/543 (2006.01)
G01N 33/557 (2006.01)

(52) U.S. Cl.
CPC ....... *G01N 27/021* (2013.01); *G01N 33/5438* (2013.01); *G01N 33/54366* (2013.01); *G01N 33/557* (2013.01); *B01L 2300/06* (2013.01); *B01L 2300/0645* (2013.01); *B01L 2300/123* (2013.01); *B01L 2400/0472* (2013.01)

(56) References Cited

U.S. PATENT DOCUMENTS

| | | | |
|---|---|---|---|
| 2008/0274493 | A1 | 11/2008 | Quake et al. |
| 2009/0011430 | A1* | 1/2009 | Ateya ............... G01N 27/3276 435/7.2 |
| 2012/0040370 | A1 | 2/2012 | Orwar et al. |
| 2015/0316502 | A1* | 11/2015 | Mohanty ............ G01N 27/4145 205/777.5 |
| 2015/0346131 | A1 | 12/2015 | Mohseni et al. |
| 2016/0252517 | A1 | 9/2016 | Lo et al. |

OTHER PUBLICATIONS

Drews, J., Drug Discovery: a historical perspective, Science 287, 1960-1964 (2000).
Durrant, J.D. et al., Molecular dynamics simulations and drug discovery, BMC Biol. 9:71 (2011).
Helmholtz, H., Über einige Gesetze der Vertheilung elektrischer Ströme in körperlichen Leitern mit Anwendung auf die thierisch-elektrischen Versuche (Some laws concerning the distribution of electrical currents in conductors with applications to experiments on animal electricity), Annalen der Physik und Chemie 165, 211-233, (1853).
Hsu, C-L et al,. A Low-Noise Gain-Enhanced Readout Amplifier for Induced Molecular Electronic Signals, IEEE, 2015, 4 pages.
Hughes, J.A. et al., Microfluidic Western blotting, Proc. Natl. Acad. Sci.109, 21450-21455 (2012).
Karns, K. et al., Microfluidic screening of electrophoretic mobility shifts elucidates riboswitch binding function, J. Am. Chem. Soc. 135, 3136-3143 (2013).
Kedziora, K.M. et al., Fluorescence Resonance Energy Transfer Microscopy (FRET), Methods Mol. Biol. 1251, 67-82 (2014).
Keller, S. et al,. High-Precision Isothermal Titration Calorimetry with Automated Peak Shape Analysis, Anal. Chem. 84, 5066-5073 (2012).
Kitagishi, K. et al., Binding between Thermolysin and Its Specific Inhibitor, Phosphoramidon, J. Biochem. 95, 529-534 (1984).
Komiyama, T. et al., Studies on inhibitory effect of phosphoramidon and its analogs on thermolysin, Arch. Biochem. Biophys. 171, 727-731 (1975).
MacBeath, G. et al., Printing proteins as microarrays for high-throughput function determination, Science 289, 1760-1763 (2000).
Malanikova, M. et al., Determination of dissociation constants of complexes of trypsin and its low molecular weight inhibitors by affinity chromatography in zonal and frontal analysis arrangement, J. Solid Phase Biochem. 2, 237-249 (1977).
Markwardt, F. et al., Comparative Studies on the Inhibition of Trypsin, Plasmin, and Thrombin by Derivatives of Benzylamine and Benzamidine, Eur. J. Biochem. 6, 502-506 (1968).
Mayer, K.M., Localized surface plasmon resonance sensors, Chem. Rev. 111, 3828-3857 (2011).
Neuzil, P. et al., Revisiting lab-on-a-chip technology for drug discovery, Nat. Rev. Drug Discov. 11, 620-632 (2012).
Pan, Y. et al., High-Throughput Electrophoretic Mobility Shift Assays for Quantitative Analysis of Molecular Binding Reactions, Anal Chem, 86, 10357-10364 (2014).
Rawlings, N.D. et al., Families of serine peptidases, Methods Enzymol. 244, 19-61 (1994).
Schoning, M.J. et al., Recent advances in biologically sensitive field-effect transistors (BioFETs), Analyst 127, 1137-1151 (2002).
Some, D., Light-scattering-based analysis of biomolecular interactions, Biophys. Rev. 5, 147-158 (2013).
Van Tassel, P.R., Statistical Mechanical Modeling of Protein Adsorption. Mat.-wiss. u. Werkstofftech. 34, 1129-1132 (2003).
Van Tassel, P.R. et al., A kinetic model of partially reversible protein adsorption. J. Phys. Chem. 106, 761-770 (1997).
Zhang, T. et al., Transient Induced Molecular Electronic Spectroscopy (TIMES) for study of protein-ligand interactions, Scientific Reports, 2016, 35570.
Zhang, T. et al., Protein-Ligan Interaction Detection with a Novel Method of Transient Induced Molecular Electronic Spectroscopy (TIMES): Experimental and Theoretical Studies, American Chemical Society, 2016, 2, pp. 834-842.
Extended European Search Report for European Patent Application No. 17764054.7, dated Oct. 28, 2019, 8 pages.
International Search Report and Written Opinion for PCT Application No. PCT/US2017/021486, dated May 30, 2017, 8 pages.
Cooper, M.A., Optical biosensors in drug discovery, Nat. Rev. Drug Discov. 1, 515-528 (2002).

\* cited by examiner

US 10,890,546 B2

TRANSIENT INDUCED MOLECULAR ELECTRONIC SPECTROSCOPY METHOD FOR STUDY OF MOLECULE INTERACTIONS

CROSS-REFERENCE TO RELATED APPLICATIONS

This patent document is a 371 National Phase Application of PCT Application No. PCT/US2017/021486 entitled "TRANSIENT INDUCED MOLECULAR ELECTRONIC SPECTROSCOPY METHOD FOR STUDY OF MOLECULE INTERACTIONS", filed on Mar. 9, 2017, which claims benefit and priority of U.S. Provisional Patent Application No. 62/305,766 entitled "TRANSIENT INDUCED MOLECULAR ELECTRONIC SPECTROSCOPY (TIMES) METHOD FOR STUDY OF PROTEIN-LIGAND INTERACTIONS," filed on Mar. 9, 2016. The entire contents of the aforementioned patent applications are incorporated by reference as part of the disclosure of this patent document.

STATEMENT REGARDING FEDERALLY SPONSORED RESEARCH OR DEVELOPMENT

This invention was made with government support under Grant Number 1610516, awarded by the National Science Foundation. The government has certain rights in the invention.

TECHNICAL FIELD

This patent document relates to systems, devices, and processes for detecting interactions between molecules, e.g., protein-ligand interactions.

BACKGROUND

Protein-ligand interaction plays the central role in biomedical process and drug discovery due to its scientific significance and practical applications. While computer simulations and high-throughput screening methods have been widely applied to perform early stage screening of drug candidates, limited methods are available to investigate the effect of interactions between molecules such as protein-ligand interaction without any external disruptions. This patent document provides techniques that, among other benefits, overcome these limitations in the field.

SUMMARY

In one aspect, this document relates to a device for measuring a transient induced molecular electronic spectroscopy (TIMES) signal of a molecule.

In one example aspect, a device for measuring a transient induced molecular electronic spectroscopy (TIMES) signal of a molecule is disclosed. The device includes a microfluidic channel, a sensing pad comprising an electrode, a low-noise amplifier circuit, at least one inlet coupled to a first end of the microfluidic channel, and at least one outlet coupled to a second end of the microfluidic channel. The electrodes are connected to the amplifier circuit.

In another example aspect, a method for detecting binding of molecules including receiving a signal generated by the dipole moment change when a first molecule and a second molecule forms a complex, performing analog-to-digital conversion of the signal to generate a digitized signal, processing the digitized signal by a processor to detect binding between the first molecule and the second molecule. In some embodiments, the first and second molecules are a protein and a ligand, respectively.

DETAILED DESCRIPTION

Figure 1:
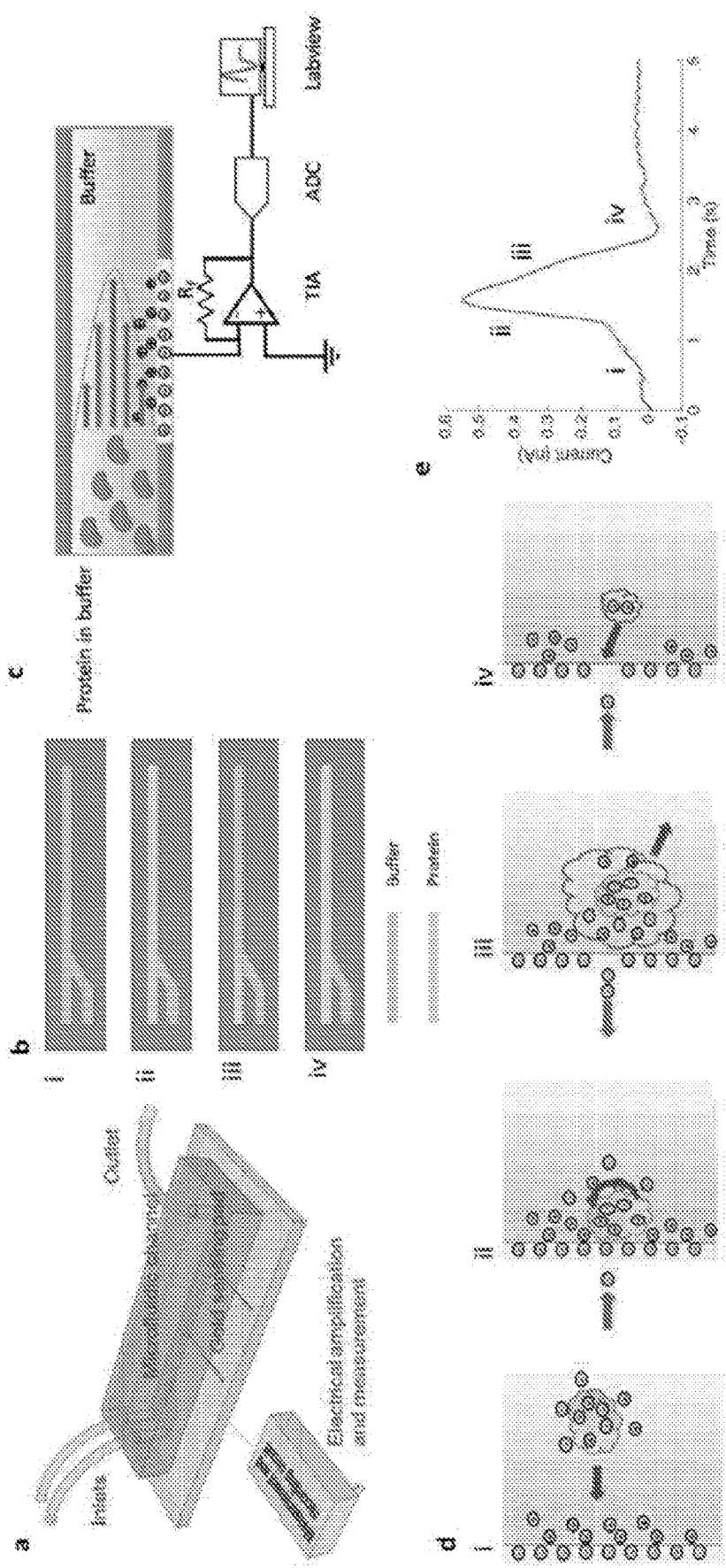
FIGS. 1(a)-1(e) show experimental setup and illustration of the physical process that gives rise to the TIMES signal. (a) 3D view of the TIMES setup consisting of a polydimethylsiloxane (PDMS)-based microfluidic channel with gold electrodes and a low-noise transimpedance amplifier circuit. (b) The top view of microfluidic channel and the experimental work flow for channel conditioning, protein loading, and testing. (b,i) Before the experiment, the channel was flushed and filled with buffer injected from both inlets. (b,ii) One of the inlets was replaced with protein (or other molecules of interest) laden buffer to fill the channel. (b,iii) The syringe pump driving protein flow was stopped and the other syringe pump driving the buffer was turned on to wash the channel. This procedure completed the conditioning of the system before test, leaving a liquid interface between protein and buffer solutions near the input of the channel. (b,iv) To start the experiment, the flow of the buffer was stopped and the protein laden solution flowed through microfluidic channel. (c) Side view schematic of laminar flow in the microfluidic channel, charge distribution at the electrode/liquid interface, and the measurement and recording circuit system. (d) Illustration of charge movement, protein reorientation, and signal generation. (d,i) Local charge neutrality was maintained while a molecule was diffused towards the gold electrode. (d,ii) Ion redistribution and protein dipole moment reorientation occurred when the protein was near the gold electrode. Charge was transferred between the gold electrode and the external circuit due to the image charge effect. (d,iii) Protein left the electrode and dragged the local ions via electrostatic interactions. (d,iv) Ions returned to the electrode and the steady state was restored. (e) The measured TIMES signal produced by 500 nM thermolysin.

Disclosed herein, among other things, is a method, referred to as Transient Induced Molecular Electronic Spectroscopy (TIMES), to detect interactions of molecules such as protein-ligand interactions without any protein engineering or chemical modification. The physics model of the TIMES signal is established and mathematical formula is generated to attain a physical insight of molecule interactions without any disturbances by molecular probes, fluorescent labels, or immobilization of molecules. For a demonstration of the functionality of this method, the TIMES signals are used to find the dissociation constants for the affinity of reactions, the shear-stress dependent adsorption time of molecules on surface, and other interesting features of interactions of molecules in native conditions. Although protein-ligand binding and detection of protein-ligand complex are used in this document as examples for studying the interactions between molecules, one of ordinary skill in the art would understand that the disclosed technology, methods and devices can be applied to study the interactions between other molecules under native conditions or in a native environment.

Protein-ligand interaction detection without disturbances (e.g., surface immobilization, fluorescent labeling, and crystallization) presents a key question in protein chemistry and drug discovery. As a unique tool, TIMES incorporates a unique design of microfluidic platform and integrated sensing electrodes to operate in a label-free and immobilization-free manner to provide crucial information for protein-ligand interactions in relevant physiological conditions, and offers a simple and effective method to investigate fundamental protein chemistry and drug discoveries.

Through experiments and theoretical simulations, it is demonstrated herein that the TIMES technique actually detects protein-ligand binding through signals generated by surface electric polarization. The accuracy and sensitivity of experiments are demonstrated by precise measurements of dissociation constant of lysozyme and N-acetyl-D-glucosamine (NAG) ligand and its trimer, $NAG_3$. Computational fluid dynamics (CFD) computation is performed to demonstrate that the surface's electric polarization signal originates from the induced image charges during the transition state of surface mass transport, which is governed by the overall effects of protein concentration, hydraulic forces, and surface fouling due to protein adsorption. Hybrid atomistic molecular dynamics (MD) simulations and free energy computation show that ligand binding affects lysozyme structure and stability, producing different adsorption orientation and surface polarization to give the characteristic TIMES signals. Although the protein-ligand interactions are used as examples, the TIMES method is a general technique that can be applied to study signals from reactions between many kinds of molecules.

Functional proteins, especially those surrounded by the liquid environment, have extraordinary complexities and degrees of freedom to form 3D structures, while their biological functions are sensitive to and can be modified substantially by their binding with molecules (i.e., ligands) that are much smaller than themselves. The abilities to quantitatively and precisely characterize protein-ligand interactions are essential to understanding and controlling protein's properties. There have been several sensing techniques for investigation of protein-ligand interactions, including surface plasmon resonance (SPR), isothermal calorimetry (ITC), biologically modified field effect transistors (BioFET), differential light scattering (DLS), fluorescence resonance energy transfer (FRET), electrophoretic mobility shift (EMSA) and small molecule microarray, etc. Most of these methods can measure binding affinity, kinetics, and other thermodynamic characteristics of protein-ligand interactions. However, there are still open and important problems not addressed by the existing methods: (i) Using fluorescent labeling on molecules in FRET, EMSA, and small molecules microarray detection methods, external modifications are added to the molecules, which could affect the binding sites or molecular structural configurations. (ii) Using surface immobilization in SPR and BioFET techniques, spatial limitation is introduced to alter the entropy of the system, which can affect the experimental results by limiting protein movements or protein folding/unfolding, and cause discrepancies from reactions in physiological conditions. (iii) Techniques such as ITC relies on heat release from the reactions have relatively low resolution, produced limited information on reaction kinetics, and face difficulties in reactions that do not generate a large amount of heat (e.g. entropy driven rather than enthalpy driven reactions). (iv) Optical methods such as DLS only work for proteins that can crystalize or produce aggregation, with other constraints on the critical temperature and concentration.

In sum, the existing methods require the formation of protein crystal or aggregate, fluorescent labeling, or surface immobilization of molecules. Given the small size of ligand molecules and the importance of protein folding in 3D space for the reactions, fluorescent labeling and molecular immobilization can introduce significant disturbances to the reactions, producing potentially incorrect or misleading results in key parameters such as reaction coefficients (e.g., dissociation constant, $K_d$). On the other hand, these label-free and immobilization-free methods that are currently available, such as ITC and differential optical scattering techniques, render low throughput and limited temporal resolution, and often work only under special conditions (e.g., protein crystallization or exothermic reactions).

The method disclosed herein, Transient Induced Molecular Electronic Spectroscopy (TIMES), can detect protein-ligand binding without the above constraints. TIMES is a label-free, immobilization-free technique, and produces accurate and repeatable results with high temporal resolution. In TIMES, the readout is related to molecular interactions with the electrode surface, whereas the reaction itself is performed in the bulk space. As a method of signal readout, the TIMES signal shows the electric response of the reaction products approaching the electrode surface connected to a low-noise electric amplifier. The TIMES method measures the signal caused by the dipole moment change when protein and ligand form protein-ligand complex, breaking new grounds for studies of protein-ligand interaction. The TIMES signal has an excellent signal-to-noise ratio and timing resolution even though the difference in the molecular weight and chemical composition between protein and protein-ligand complex could be very small, sometimes less than 1%. The TIMES method produces signals related to the dipole moment and charge distribution of molecules, thus providing not only undisturbed signal in physiological conditions but also signals revealing molecular properties unattainable by and complementary with the existing methods including FRET, SPR, etc. Some characteristics and functions of the TIMES signals, include but are not limited to, measurements of reaction dissociation constants between proteins and ligands.

Disclosed herein through experiments and physical computations are four aspects: (a) The accuracy of the TIMES technique is demonstrated by measuring the dissociation constant of lysozyme protein with N-acetyl-D-glucosamine (NAG) and its trimer, N,N',N"-triacetylchitotriose (NAG$_3$) ligands, and showing that the dissociation coefficient of protein-ligand complex made of the same type of molecule can differ by 3 orders of magnitude. (b) Aided by an analytical model and detailed computational fluid dynamics (CFD) calculations, it is shown that the measured TIMES signal is directly proportional to the induced charge of a protein molecule (or protein-ligand complex) approaching the electrode. (c) The macroscopic level molecular transfer in a microfluidic channel is related to the microscopic molecular interfacial mass transfer by incorporating the effect of hydraulic forces and surface's biofouling (i.e., protein adsorption and desorption from the electrode surface subject to the flow induced shear stress). (d) Full-atom molecular dynamics (MD) simulation combined with binding free energy computation is performed to elucidate the fundamentals of the electric signal, which is related to the adsorbed protein's charge distribution (such as net charge, dipole moment, etc.) and surface polarization at the microscopic level. Through these efforts, the feasibility is demonstrated and the physical foundation of the TIMES technique is established as a method to investigate protein-ligand interactions without labeling or immobilization.

TIMES Measurements of Dissociation Constant

To create a flux of protein molecules towards the electrode, a microfluidic device can be used to produce a concentration gradient along the height of the channel. In the TIMES setup (FIG. 1a), the microfluidic channel has two inlets, one for the buffer solution and the other for introducing the molecule of interest (i.e. protein molecule or mixtures of protein and ligand) and one outlet. In some embodiments, a single inlet may be used and the buffer solution and the molecule of interest may be introduced one after another. The entire channel is at first filled up with the buffer solution and then the molecule of interest is introduced from another inlet (FIG. 1b). For a laminar flow, the travel speed at the center of the channel is the greatest and approaches zero at the channel wall where the gold electrode is located (FIG. 1c). As a result, a concentration gradient between the center of the channel (having the highest and constant molecular concentration) and the electrode surface can be established. Such concentration gradient produced a diffusion flux for the molecules towards the electrode to produce the TIMES signal.

Along the microfluidic channel there are gold electrodes connected to an external amplifier circuit. A molecule carrying a dipole moment in the buffer solution can interact with the electric field near the solution/electrode interface within the Debye length, which is in the order of 1 nm for typical ionic strength. The interfacial electric field, approximately equal to the Zeta potential divided by the Debye length according to the double-layer model can "orient" the molecule according to its charge state and dipole moment to minimize the free energy. As the molecules are oriented by the surface field, an induced dipole develops due to the mirror effect of the metallic surface. In the near field condition, dipole moment of a macromolecule such as protein has the dominant effect over the net charge of the molecule, and the alignment of the dipole moment with the surface field produces a charge transfer between the gold electrode contacting the fluid and the measurement circuit system in FIG. 1c. Such charge transfer induces an electric current that is amplified and converted into a voltage signal by a transimpedance amplifier (TIA). The low-noise amplifier can a transimpedance amplifier, and the transimpedance can be greater than 1 Mohm.

After converting the analog signal to digital signal through an analog-to-digital converter (ADC), the real-time signal originated by the field-induced dipole orientation of the molecules can be recorded. In the test system, protein is the only macromolecule that possesses a large dipole moment (Table 1), and all other ions in the buffer move around the protein to minimize the free energy of the system. Hence the detected signal is primarily produced by protein or protein-ligand complex near the electrode. Although in many cases the ligand molecular weight could be significantly less than the molecular weight of the protein, the formation of protein-ligand complex can alter the 3D configuration of the protein molecule, thus changing the dipole moment and charge distribution appreciably. The TIMES method monitors the native protein ligand interactions requiring no immobilization or labelling and with high temporal resolution. Next the physical principle that produces the TIMES signal is described.

TABLE 1

PDB-ID and calculated dipole moment of proteins

| Protein | trypsin | thermolysin | p-ABA | phosphoramidon |
|---|---|---|---|---|
| Molecular Weight (D) | 24.4k | 34.6k | 135 | 543 |
| Charge (e) | 6 | −10 | 2 | −2 |
| Dipole (μ/D) | 353 | 547 | 3.28 | 3.71 |

It is assumed that with sufficient ionic strength in the buffer, the "local charge neutrality" condition is satisfied when protein travels in solution without an external field (FIG. 1d, i). Local charge neutrality assumes that charges on the surface of protein are neutralized by the mobile counter charges in the buffer within a time scale of "dielectric relation time" equal to $\varepsilon/\sigma$ where $\varepsilon$ and $\sigma$ are the permittivity and conductivity of the buffer solution. Since the dielectric relaxation time is typically 1 to 100 ns, much shorter than the time scale of interest in the measurement, the local charge neutrality condition can be satisfied everywhere in the solution (FIG. 1d) except for regions right next to the electrode/liquid interface where the electric field is present. When the protein molecules approach the electrode and experience the electric field from the Zeta potential, two things take place: at first those mobile ions around the protein to maintain local charge neutrality are stripped off by the E-field and find their new equilibrium distributions, and secondly the protein molecules are oriented to have their dipole moment aligned to the direction of the field (FIG. 1d, i). The alignment of dipole moment of protein gives rise to an induced charge flow between the electrode and the amplifier input, giving rise to a detectable signal (FIG. 1d, ii). Driven by the shear stress of the laminar flow in the microfluidic channel, the protein molecules may not permanently be adsorbed to the electrode surface but detached from the gold electrode after some period of time. The departing molecules carry neighboring ions with them via electrostatic interactions and drag force, disturbing the local ion distribution and generating an overshoot in the electric signal (FIG. 1d, iii). Eventually, those ions carried by the departing proteins return to the electrode surface and the steady state is restored (FIG. 1d, iv). The TIMES signal produced by 500 nM thermolysin molecules is shown in FIG. 1e. Similar analysis and model of protein-surface interaction have been reported before[22, 23]. The theory and mathematical formulation of TIMES signal is described next.

It is assumed that q(t) is the induced charge in the gold electrode in response to a protein molecule reaching the electrode surface. q(t) can be treated as the "impulse response" or the "Green's function" generated by a single protein (or protein/ligand complex) molecule approaching the electrode, having the unit of "Coulomb". The net charge signal on the electrode, induced by all the protein molecules at a specific time, can be represented as $$S(t) = A \int_0^t q(u) J(t-u) du \qquad (1)$$

where A is the area of the electrode and J(t) is the flux of the protein molecules at the electrode. The flux of molecule can be represented as $$J(t) = J_+(t) - J_-(t) \qquad (2)$$

where $J_+$ and $J_-$ are the flux of molecular adsorption and desorption, respectively.

The expression for the protein concentration immediately next to the electrode surface, $n_i(t)$, which is related to the protein concentration outside the Debye length where the electric field is nearly zero, is calculated as follows:

$$n_i(t) = n(0, t) e^{\frac{-Ze\zeta}{kT}} = \gamma n(0, t) \qquad (3)$$

where Ze is the charge of the protein and $\zeta$ is the zeta potential. Throughout the analysis, it is assumed that the protein concentration is low enough not to change the ionic strength of the buffer. Therefore, the zeta potential is not changed significantly by the protein so $\gamma$ can be treated as a constant and its value is determined by the electrode material and the buffer solution.

The transport of protein across the channel thickness is governed by the equation:

$$\frac{\partial n(x, t)}{\partial t} = D \frac{\partial^2 n}{\partial x^2}$$

with the boundary conditions: $n(x=L, t) = n_o$ and $$\frac{\partial n}{\partial x}\bigg|_{x=0} = 0$$

where x=L is the center of the microfluidic channel (i.e. the channel height is 2 L). The analytical solution for n(0, t) at the position just outside the Debye length (i.e. E-field is nearly zero) is obtained as $$n(x=0, t) = \left[ n_o - \sum_{M=0}^{\infty} \frac{4 n_o (-1)^M}{(2M+1)\pi} e^{\frac{-(2M+1)^2 Dt}{4L^2}} \right] t > 0 \qquad (4)$$

The detailed derivation is as follows: Assume that each time a protein hits the electrode surface, it will induce a charge on the gold electrode it contacts: q(t). q(t) has the unit of Coul. The protein may stay on the electrode surface or leaves the surface after a time period $\tau_s$. The net charge signal produced by all the protein molecules at a specific time becomes $$S(t)=A\int_0^t q(t-u)J(u)du=A\int_0^t q(u)J(t-u)du \quad (A)$$

where J(t) is the net flux of protein towards the electrode, having the unit: #/Area-s.

Taking the time derivative of (1), it is obtained $$\frac{dS(t)}{dt} = Aq(t)J(0) + A\int_0^t q(u)\left[\frac{d}{dt}J(t-u)\right]du \quad (B)$$

$$\frac{dS(t)}{dt}$$

is the amount of protein-induced current (unit: Amp).

The fluid is divided into two regions: region 1 covers the entire space in the microfluidic channel and region 2 is the proximity to the surface of the electrode, typically within the Debye length of the thickness of around 1 nanometer. Since there exists no electric field in region 1 and because of the laminal flow, the protein concentration away from the electrode interface is governed by the diffusion equation due to protein concentration gradient. There is $$\frac{\partial n}{\partial t} = D\frac{\partial^2 n}{\partial x^2} \quad (C)$$

with the boundary conditions:

$$n(t, x = L) = n_o \text{ for } t \geq 0 \quad (D)$$
$$\frac{\partial n(t, x = 0)}{\partial x} = 0 \text{ for } t \geq 0$$
$$n(t = 0, x) = 0 \text{ for } 0 \leq x < L$$

Figure 11:
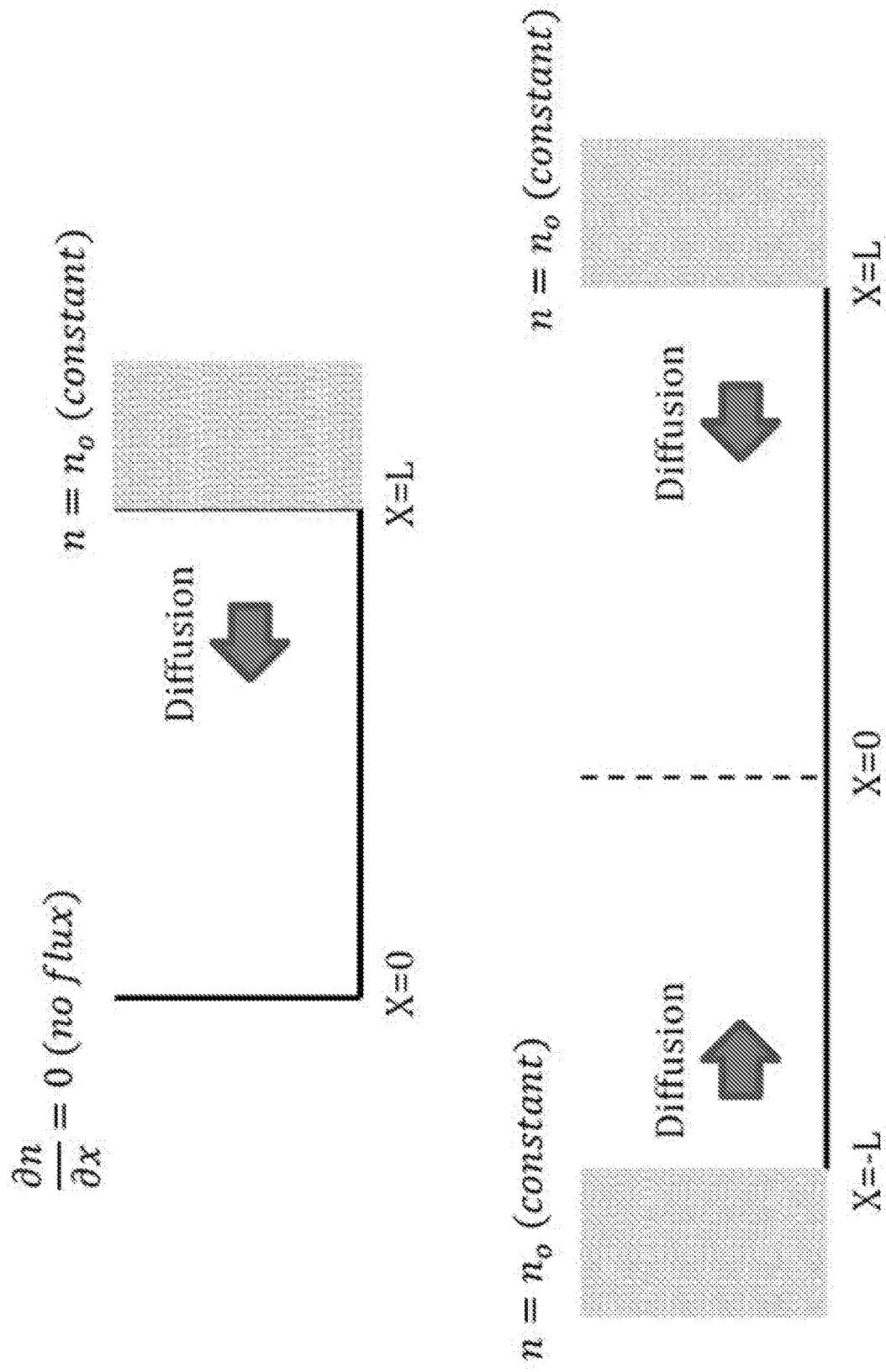
FIG. 11 shows diagram of different boundary conditions used in the physical model.

As shown in FIG. 11, the problem in (D) is equivalent to the problem in (E) with different boundary conditions:

$$n(t,x=L)=n_o \text{ for } t\geq 0$$
$$n(t,x=-L)=n_o \text{ for } t\geq 0$$
$$n(t=0,x)=0 \text{ for } -L<x<L \quad (E)$$

Assume $u(x,t)=T(t)x(x)$ is a solution for (C)

$$\frac{1}{T(t)}\frac{dT(t)}{dt} = \frac{D}{X(x)}\frac{d^2X(x)}{dx^2} = -k$$

$$u(x, t) = e^{-kt}\left[C_k\cos\left(\sqrt{\frac{k}{D}}x\right) + E_k\sin\left(\sqrt{\frac{k}{D}}x\right)\right]$$

The general solution can be represented as $$n(x, t) = n_o - \sum_k e^{-kt}\left[C_k\cos\left(\sqrt{\frac{k}{D}}x\right) + E_k\sin\left(\sqrt{\frac{k}{D}}x\right)\right] \quad (F)$$

Using the boundary conditions in (E), there is $$\frac{\partial n(x = 0, t)}{\partial x} =$$

$$0 = \sum_k \sqrt{\frac{k}{D}} e^{-kt}\left[-C_k\sin\left(\sqrt{\frac{k}{D}}x\right) + E_k\cos\left(\sqrt{\frac{k}{D}}x\right)\right]_{x=0} \text{ for } t > 0$$

This means $E_k$'s=0

$$n(x, t) = n_o - \sum_k e^{-kt}\left[C_k\cos\left(\sqrt{\frac{k}{D}}x\right)\right] \quad (G)$$

Also from (E) it is required $$n(x = \pm L, t) = n_o - \sum_k e^{-kt}\left[C_k\cos\left(\sqrt{\frac{k}{D}}L\right)\right] = n_o \text{ for } t > 0$$

Then there is $$\sqrt{\frac{k}{D}}L = \left(M + \frac{1}{2}\right)\pi$$

$$M: -\infty, \ldots, \infty$$

$$n(x, t) = n_o - \sum_{M=-\infty}^{\infty} e^{-\frac{(M+1/2)^2 Dt}{L^2}} C_M\cos\left(\frac{\left(M + \frac{1}{2}\right)\pi x}{L}\right) \text{ for } t \geq 0$$

The above equation can be simplified as $$n(x, t) = n_0 - \sum_{M=0}^{\infty} C'_M e^{-\frac{(2M+2)^2 Dt}{4L^2}} \cos\left(\frac{(2M + 1)\pi x}{2L}\right) \text{ for } t \geq 0 \quad (H)$$

At t=0, $$n(x, t = 0) = 0 = n_o - \sum_{M=0}^{\infty} C'_M \cos\left(\frac{(2M + 1)\pi x}{2L}\right) \text{ for } -L < x < L \quad (I)$$

$$C'_M = \frac{n_o \int_{-L}^{L}\cos\left(\frac{(2M + 1)\pi x}{2L}\right)dx}{\int_{-L}^{L}\cos^2\left(\frac{(2M + 1)\pi x}{2L}\right)dx} = \frac{4n_o(-1)^M}{(2M + 1)\pi} \quad (J)$$

Hence $$n(x, t) = n_o - \sum_{M=0}^{\infty} \frac{4n_o(-1)^M}{(2M + 1)\pi} e^{-\frac{(2M+1)^2 Dt}{4L^2}} \cos\left(\frac{(2M + 1)\pi x}{2L}\right) \quad (K)$$

To find out n(x=0,t)

$$n(0, t) = n_o - \sum_{M=0}^{\infty} \frac{4n_o(-1)^M}{(2M+1)\pi} e^{\frac{-(2M+1)^2 Dt}{4L^2}} \quad (L)$$

Note that (L) is the protein concentration in region 1 where there is no electric field. At the surface of the electrode, the protein concentration can be approximated as $$n_t(t) = \quad (M)$$

$$n(0, t)e^{\frac{-Ze\zeta}{kT}} = \left[n_o - \sum_{M=0}^{\infty} \frac{4n_o(-1)^M}{(2M+1)\pi} e^{\frac{-(2M+1)^1 Dt}{4L^2}}\right] e^{\frac{-Ze\zeta}{kT}} = \gamma n(0, t)$$

$$\gamma = e^{\frac{-Ze\zeta}{kT}}$$

where Ze is the charge of the protein and $\zeta$ is the zeta potential. It is assumed that the protein concentration is low enough not to change the ionic strength of the buffer. Therefore the zeta potential is not changed significantly by the protein.

Note that $$n(x = 0, t) = \left[n_o - \sum_{M=0}^{\infty} \frac{4n_o(-1)^M}{(2M+1)\pi} e^{\frac{-(2M+1)^2 Dt}{4L^2}}\right] \sim n_o$$

if the time of interest is greater than $$\frac{4L^2}{D}$$

where D is the diffusivity of protein (or protein-ligand complex).

In equation (2), $$J_+(t) = K_+ n_i(t)(1-\theta) \quad (5)$$

$K_+$ has the unit of velocity.
$\theta$: fraction of monolayer deposition $0 \leq \theta \leq 1$.

$$J_-(t) = K_- \theta \quad (6)$$

$K_-$ has the unit of flux (1/s-area).
At equilibrium (i.e. t→∞), $$J_+(\infty) = K_+ n_i(\infty)(1-\theta_o) = K_+ n_o \gamma(1-\theta_o) = K_- \theta_o \quad (7)$$

Using the relations in Eqs. 5-7, $$\theta(t) = \frac{\int_0^t J(u)du}{\int_0^\infty J(u)du} = \frac{K_+}{\theta_o} \frac{\int_0^t [n_i(u)(1-\theta)\theta_o - n_i(\infty)(1-\theta_o)\theta]du}{\int_0^\infty J(u)du} \quad (8)$$

Under the approximation that the time scale of interest is significantly longer than the diffusion time $$\left(\text{i.e. } t > \frac{4L^2}{D}\right),$$

Eq. (8) can be approximated as $$\theta(t) \sim \frac{K_+}{\theta_o} n_i(\infty) \frac{\int_0^t [\theta_o - \theta]du}{\int_0^\infty J(u)du} = \left(\frac{K_+ \gamma n_o}{\int_0^\infty J(u)du}\right) \int_0^t \left[1 - \frac{\theta}{\theta_o}\right] du \quad (9)$$

And the induced charge on the electrode by a protein molecule is obtained as $$q(t) = \left[\frac{1}{A(K_+ \gamma n_o)}\right]\left[i(t) + \frac{1}{\tau_S}\int_0^t i(u)du\right] \quad (10)$$

$$\tau_S = \frac{\theta_o \int_0^\infty J(u)du}{K_+ \gamma n_o} = \frac{\int_0^\infty J(u)du}{K_- + K_+ \gamma n_o} \quad (11)$$

where $n_o$ is the protein concentration at equilibrium, and $\tau_s$ has the physical meaning of the average dwelling time or surface adsorption time for a protein (or protein-ligand complex) molecule on the surface of electrode.

From (10), it is shown that the transient induced molecular current, i(t), can be used to find (a) the induced charge, q(t), by each molecule when approaching the electrode surface and (b) the surface adsorption time ($\tau_s$) of the molecule on the electrode surface without any molecular labeling or surface immobilization.

Figure 2:
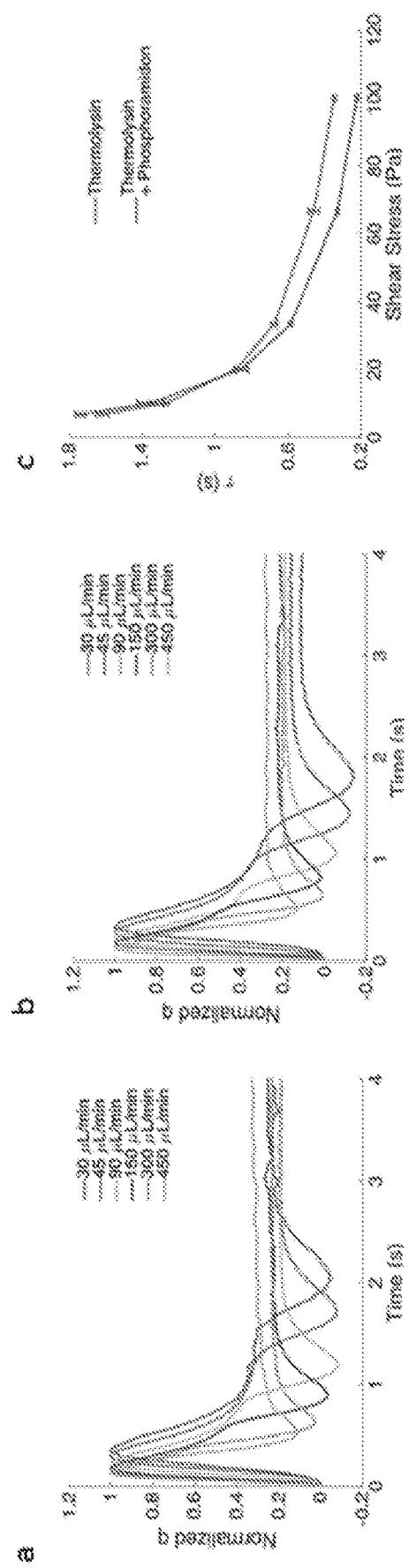
FIGS. 2(a)-2(c) show induced charge response q(t). and the adsorption time $\tau_s$, of a single protein or protein/ligand complex under different flow rates (shear stress) obtained from the TIMES signal using Eq. (2). Induced charge response by thermolysin (a) and thermolysin/phosphoramidon complex (b) under different flow rate (shear stress) from 30 μL/min (6.67 Pa) to 450 μL/min (100 Pa). (c) Shear stress dependent surface adsorption time of thermolysin and thermolysin/phosphoramidon complex.

The concepts using a protein-ligand pair are demonstrated as an example. Thermolysin is a 34.6 KD thermostable metalloproteinase produced by the Gram-positive bacteria *Bacillus thermoproteolyticus*. It preferentially cleaves at the N-terminus of the peptide bonds containing hydrophobic residues such as leucine, isoleucine, and phenylalanine. Phosphoramidon was isolated from *Streptomyces tanashiensi*, which inhibits thermolysin specifically. The normalized induced charge, q(t), by thermolysin before and after binding with phosphoramidon under different flow rate is shown in FIGS. 2a and 2b. The shear stress dependent surface adsorption time of thermolysin before and after binding with phosphoramidon is compared in FIG. 2c.

From FIG. 2a, the surface adsorption time of thermolysin decreases monotonically with increasing flow rate because a higher flow rate in the microfluidic channel produces greater shear stress according to Poiseuille's Law to remove protein from the electrode surface, thus reducing the average adsorption time of protein molecules on the electrode. The same trend was observed for thermolysin/phosphoramidon complex (FIG. 2b). However, thermolysin and thermolysin/phosphoramidon show different adsorption time dependence on the flow induced shear stress, as shown in FIG. 2c. The results provide clear evidences that in spite of very similar molecular weight and size of the protein and protein/ligand complex, the binding strength of the two molecules to the electrode show appreciable differences, manifested in the adsorption times measured from the TIMES signals.

Under the condition that the system consists of more than one type of molecules (e.g. coexistence of protein, ligand, and protein-ligand complex), then the measured TIMES signal can be further approximated by (12) when the second term in (10) becomes negligible. This approximation is valid when the time of concern is shorter than the protein adsorption time $\tau_s$.

$$i(t) \sim A \sum_i n_{o,i} v_{s,i} \gamma_i q_i(t - t_{oi}) \quad \text{where} \quad t_{oi} = \frac{4L^2}{D_i} \quad (12)$$

In the case of first-order reaction: Ligand+Protein↔PLcomplex $$K_D = \frac{n_L \, n_P}{n_C}$$

where $n_L$, $n_P$, $n_C$ represent the equilibrium concentration of ligand, protein, and protein-ligand complex, respectively.

Assuming all $t_{oi}$'s are short compared to the timing resolution of the measurement system, (12) can be approximated as $$i(t) \sim A[n_{o,P} v_{s,P} \gamma_P q_P(t) + n_{o,L} v_{s,L} \gamma_L q_L(t) + n_{o,c} v_{s,c} \gamma_c q_c(t)] \quad (13)$$

Before reaction, the initial protein and ligand concentrations are assumed to be x and y, respectively. After the equilibrium is reached,
$n_{o,P} = x - z$, $n_{o,L} = y - z$, $n_{o,c} = z$
Substituting these relations into (13), $$i(t) \sim A[[(x-y-K_D) + \sqrt{(x+y+K_D)^2 - 4xy}]G_P(t) + [(y-x-K_D) + \sqrt{(x+y+K_D)^2 - 4xy}]G_L(t) + [(x+y+K_D) - \sqrt{(x+y+K_D)^2 - 4xy}]G_c(t)] \quad (14)$$

In (14) the TIMES signal i(t) is measured under given values of x and y are known from different mixtures of protein and ligand. Since there are four unknowns: $K_D$, $G_P(t)$, $G_L(t)$, and $G_c(t)$ in (14), TIMES signals in 4 different combinations of protein ligand concentrations (e.g. protein only, ligand only, 1:2 and 2:1 protein/ligand ratios) need to be measured to solve these unknowns. Among the four unknowns, only $K_D$ is time independent, hence ideally the same value of $K_D$ at each time point should be obtained when the unknowns are solved. However, when noise added to (14) as a random variable, it causes fluctuation of $K_D$ obtained at each time point. At a sampling rate of 1 ms over 1 s period, 1000 values of $K_D$ can be obtained. Therefore a histogram of $K_D$ value can be generated to help determine its mean value to minimize the effect of noise. It is recommended that at least in two of 4 experimental conditions, x and y should be in the same order of $K_D$ (i.e., 0.1 $K_D$<x,y<10 $K_D$) to minimize the influence of noise. When there is no prior knowledge about the order of magnitude of $K_D$, x and y can be chosen arbitrarily and the choice can be examined from the histogram of $K_D$. Both the obtained value of $K_D$ and the distribution of the histogram can clearly indicate the appropriateness of the initial choice. Normally in one iteration, the proper range of x, y (i.e., protein and ligand concentration before reaction) that yields accurate $K_D$ can be found.

TIMES signals are used to find the dissociation constant of protein-ligand interactions nonmetal-dependent and metal-dependent enzymes: (a) trypsin and p-aminobenzamidine (p-ABA), (b) thermolysin and phosphoramidon.

Figure 3:
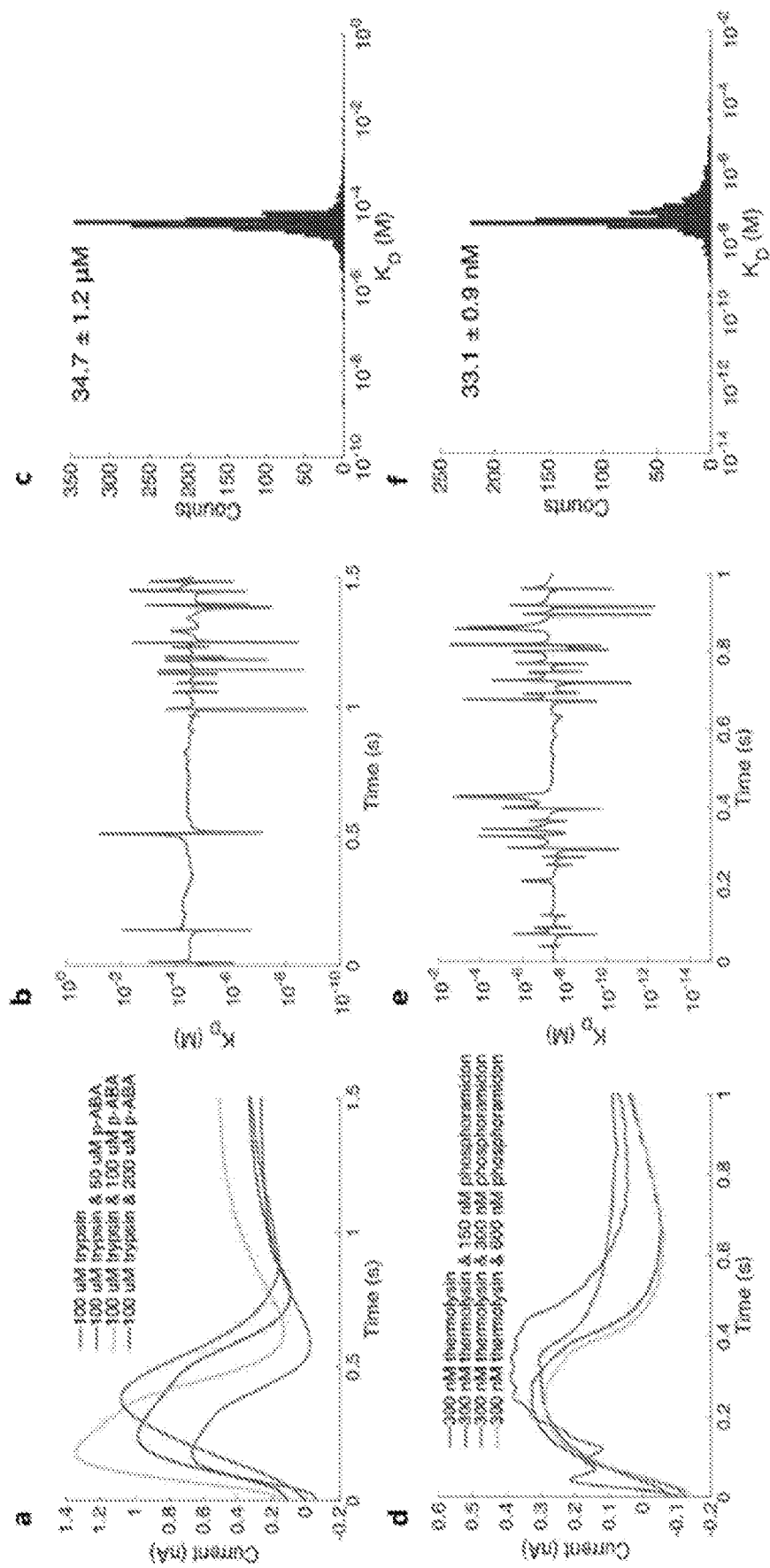
FIGS. 3(a)-3(f) show TIMES signals with different ratios of protein ligand concentrations. 5 mM Tris-HCl buffer was used for all the experiments. Solutions with different concentrations of protein and ligand were mixed under room temperature for 3 hours before running the experiment. (a) Signals from 100 uM trypsin mixed with 0, 50, 100, and 200 μM of p-ABA. (b) The calculated equilibrium dissociation constant $K_D$ from TIMES signals using Eq. (3). (c) Histogram of $K_D$ for trypsin and p-ABA reaction from 1000 data points over the 1 s measurement period. The mean value of $K_D$ is also shown in the figure. (d) Signals from 300 nM thermolysin mixed with 0, 150, 300, and 600 nM of phosphoramidon. (e) The calculated equilibrium dissociation constant $K_D$ from TIMES signals using Eq. (3). (f) Histogram of $K_D$ for thermolysin and phosphoramidon reaction from 1000 data points over the is measurement period. The mean value of $K_D$ is also shown in the figure.
Figure 4:
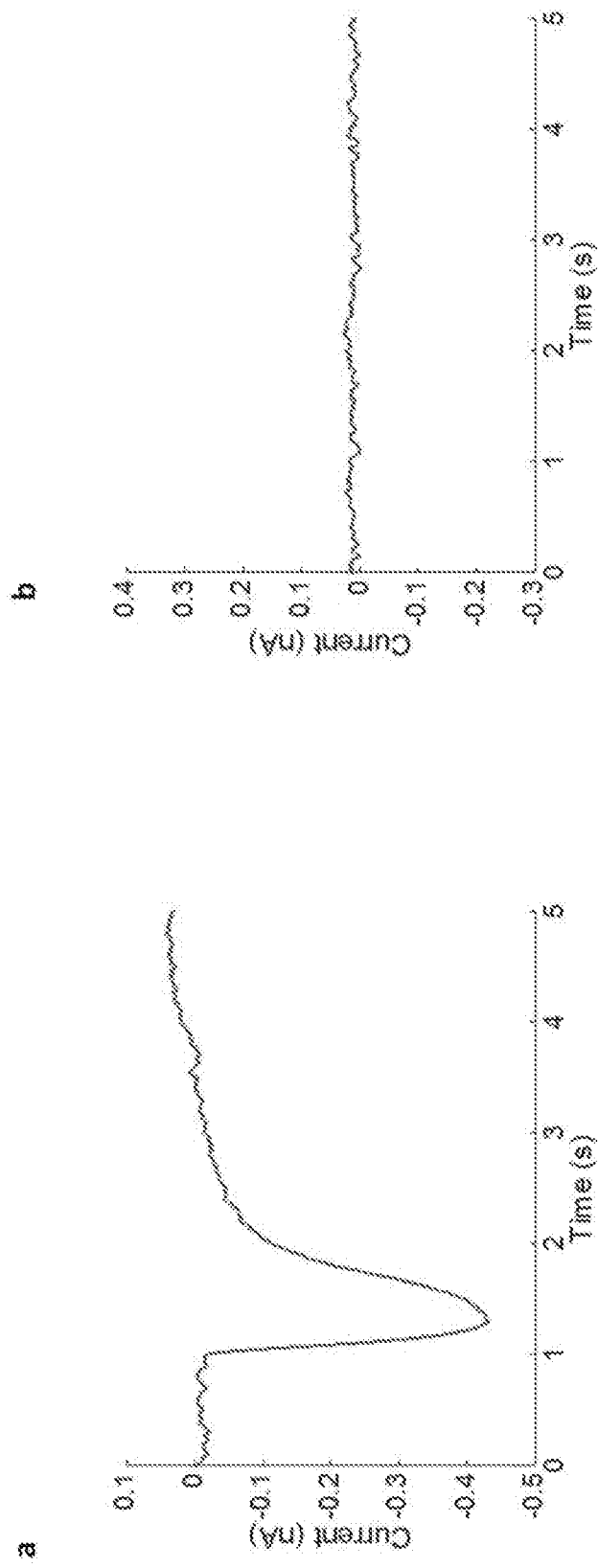
FIGS. 4(a)-4(b) show control experiments. (a) Signal showing the opposite polarity to the signal in FIG. 2d with a reversed protein concentration gradient. To reverse the protein concentration gradient, the channel was first filled with 500 nM thermolysin in 5 mM Tris-HCl buffer and then the same buffer without protein was flowed into the microfluidic channel to drive the protein away from the electrode. (b) Signal generated by protein-free buffer flowed into the microchannel filled with the same 5 mM Tris-HCl buffer. The absence of detectable signal supports that the observed TIMES signal was produced by protein instead of other side effects.
Figure 5:
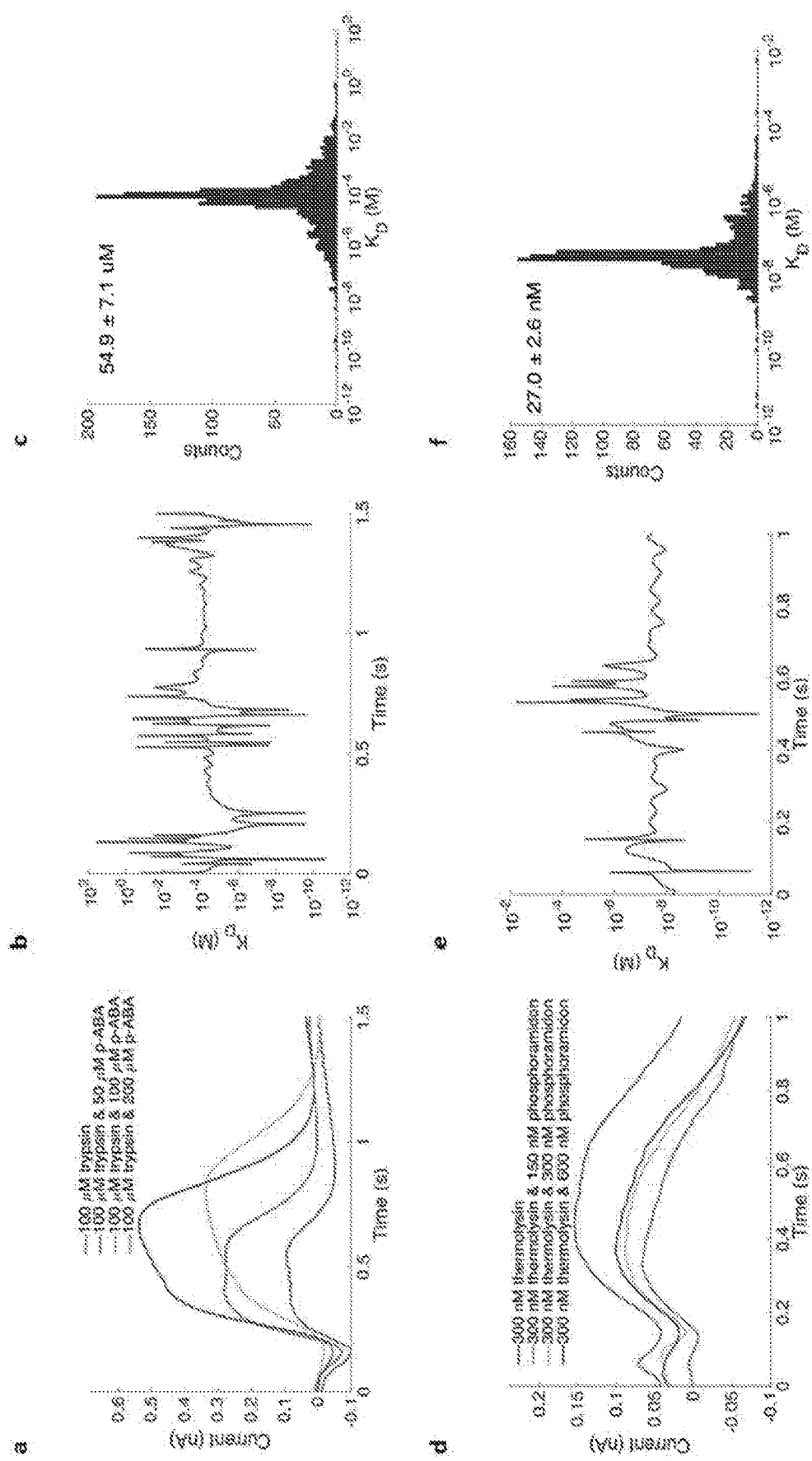
FIGS. 5(a)-5(f) show TIMES signal in Hepes buffer. (a)-(c). Trypsin and pABA, with $K_D$ calculated to be 54.9 uM. (d)-(f). Thermolysin and phosphoramidon, with $K_D$ calculated to be 27.0 nM.
Figure 6:
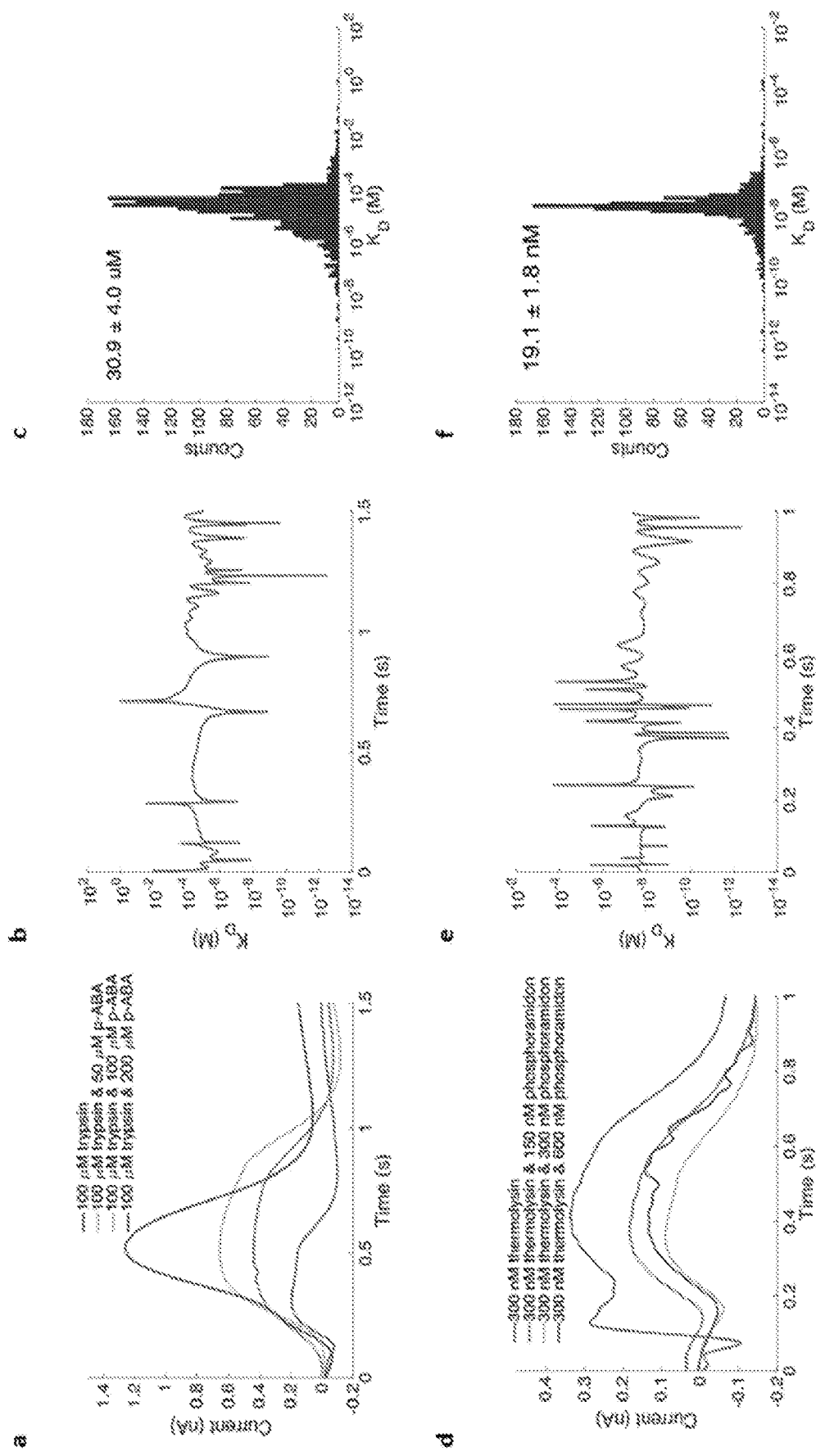
FIGS. 6(a)-6(f) show TIMES signal in 5 mM Mops buffer. (a)-(c). Trypsin and pABA, with $K_D$ calculated to be 30.9 uM. (d)-(f). Thermolysin and phosphoramidon, with $K_D$ calculated to be 19.1 nM.

Trypsin is a serine protease that hydrolyzes proteins in the vertebrate digestive system. TIMES signals were measured by adding different amounts of p-ABA to the trypsin solution (FIG. 3a). What particularly intriguing is that samples with different amounts of p-ABA generate TIMES signals that are markedly different from the trypsin signal, indicating that formation of trypsin/p-ABA complex can appreciably alter its charge distribution and dipole moment even though p-ABA is a much smaller molecule than trypsin. By measuring the TIMES signals produced by different ratios of trypsin and p-ABA in the mixtures, Eq. (3) can be used to (a) find the impulse response or Green's function q(t) for the protein-ligand complex as well as the reaction dissociation coefficient $K_D$ at each time point, as shown in FIG. 3b. The spikes in the plot of $K_D$ vs. time are caused by noise added to Eq. (14). Those spikes are outliers in the histogram plot of $K_D$ in FIG. 3c, and the most likely value in the histogram is used to be the value of $K_D$, which is found to be 34.7 μM. Three repeated runs were performed, and the averaged value agrees with the reported $K_D$ from literatures (Table 2). The minor difference could be due to different buffers and pH value in different experiments (5 mM Tris-HCl buffer at pH=7.4 was used). In the experiment with another protein ligand pair: thermolysin and phosphoramidon, the TIMES signals were obtained as shown in FIG. 3d, with $K_D$ calculated in FIGS. 3e, 3f to be 33.1 nM. Repeated experiments showed the averaged $K_D$ value to be 32.1 nM, which is in excellent agreement with the reported values (Table 2). The tests were also performed in Hepes buffer and Mops buffer under same temperature and pH, with results shown in FIGS. 4-6. The above examples demonstrate that from the TIMES signals, one can investigate protein-ligand binding with a wide range of equilibrium dissociation constants from μMs to nMs. Limited by the noise of transimpedance amplifier, the lowest dissociation constant can be measured with the current setup is ~1 nM.

TABLE 2

Summary of measured dissociation constant from TIMES and literatures

| Protein-ligand pairs | Measured $K_D$ from TIMES | Reported $K_D$ from literatures |
|---|---|---|
| Trypsin and p-ABA | 39.1 ± 3.6 μM | 12 uM (Markwardt et al.)[24] |
| | | 19 uM (Malanikova et al.)[25] |
| Thermolysin and phosphoramidon | 32.1 ± 1.9 nM | 23 nM (Kitagishi et al. 1984)[21] |
| | | 28 nM (Komiyama et al. 1975)[26] |

TABLE 3

Summary of measured dissociation constant of two protein ligand pairs from TIMES in three different buffers

| Protein-ligand pairs | Buffers | Measured $K_D$ from TIMES |
|---|---|---|
| Trypsin and p-ABA | Tris | 39.1 ± 3.6 μM |
| | Hepes | 54.9 ± 7.1 μM |
| | Mops | 30.9 ± 4.0 μM |
| Thermolysin and phosphoramidon | Tris | 32.1 ± 1.9 nM |
| | Hepes | 27.0 ± 2.6 nM |
| | Mops | 19.1 ± 1.8 nM |

Figure 7:
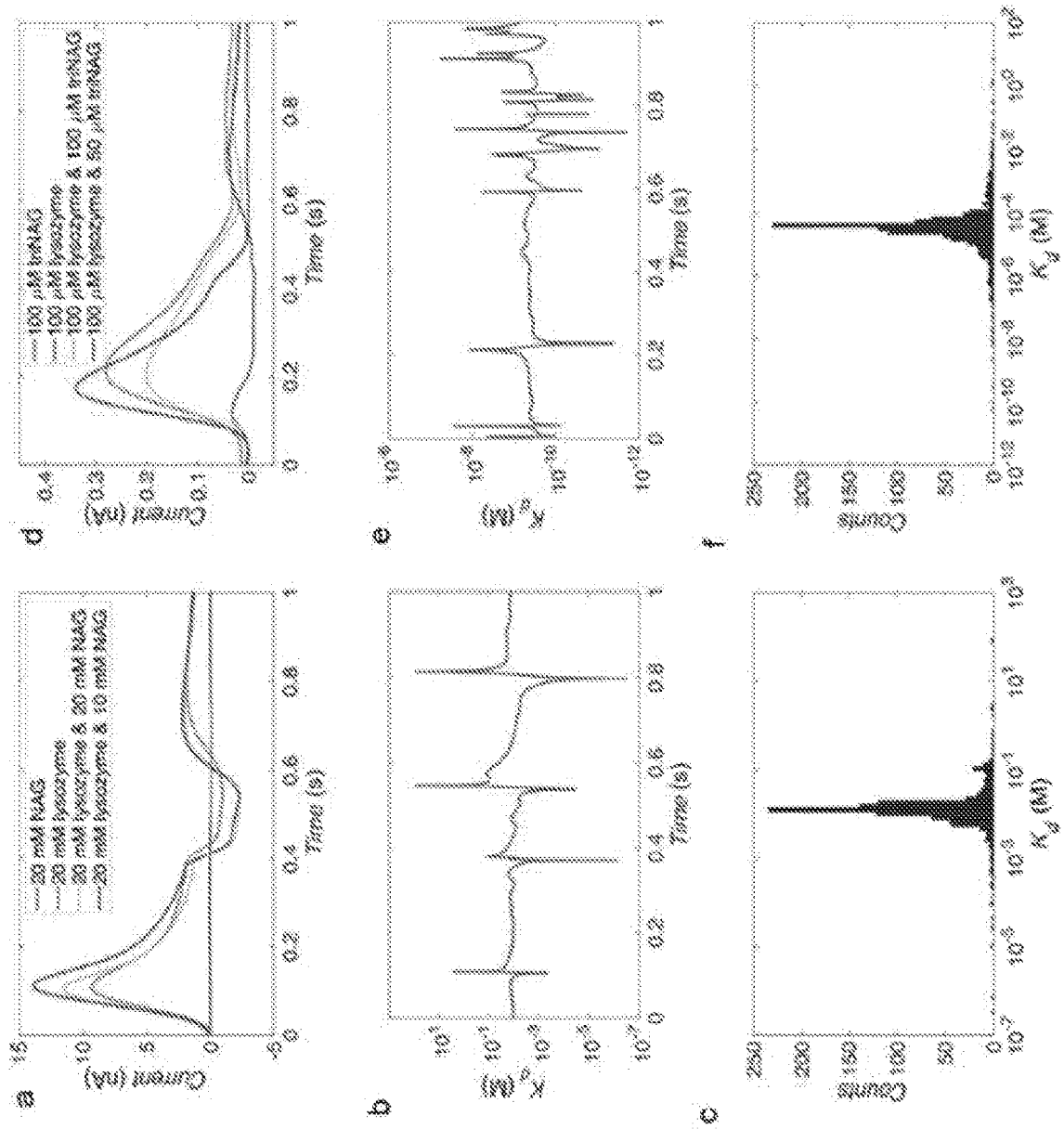
FIGS. 7(a)-7(f) show binding between lysozyme and NAG, tested in 1×PBS buffer pH=7.4 by TIMES: (a) current vs time, (b) calculation of Kd, and (c) histogram of Kd. Binding between lysozyme and $NAG_3$, tested in 1×PBS buffer pH=7.4 by TIMES: (d) current vs time, (e) calculation of Kd, and (f) histogram of Kd.

TIMES experimental measurements of protein-ligand binding dissociation constant (Kd) are shown in another example. FIG. 7 shows the measured results of the dissociation constants between lysome and two ligands: NAG and $NAG_3$. According to the analytical model disclosed herein, the measured signal of TIMES system can be represented as $$i(t) \sim A \sum_i n_{o,i} K_{+,i} \gamma_i q_i(t - t_{oi}) = A \sum_i n_{o,i} K_{+,i} \gamma_i Q_i(t - t_{oi}) \quad (15)$$

with the electrode area A, volume concentration of molecules (protein, ligand, or protein-ligand complex) $n_{o,i}$ rate of molecular adsorption to the electrode surface $K_{+,i}$, the coefficient $$\gamma_i = \exp\left(\frac{-Z_i e \zeta}{kT}\right)$$

with $\zeta$ being the zeta potential, molecular induced charge as a function of time $q_i(t-t_{oi})$, $Q_i(t-t_{oi}) = \gamma_i q_i(t-t_{oi})$, and diffusion time $$t_{oi} = \frac{4L^2}{D_i}$$

for the molecule to transport transversely toward the electrode.

Utilizing electric signals for ligand, protein, and protein-ligand complex, protein-ligand dissociation constant can be obtained to estimate protein-ligand dissociation coefficient (Kd), $$K_d = \frac{n_L n_P}{n_C} \quad (16)$$

where $n_L$, $n_P$, and $n_C$ represent the bulk concentration of ligand, protein, and complex, respectively, in the unit of mol/L. FIG. 7a shows TIMES signals for different ratios of lysozyme and NAG. A total of 4 unknowns are to be found: the time-dependent induced charge response by the protein, ligand, and protein-ligand complex, namely, $Q_P(t)$, $Q_L(t)$, and $Q_{P-L}(t)$ in (15), and the dissociation constant, $K_d$. To find all these values, an experiment was performed by flowing four samples through the device: for example, samples containing protein only, ligand only, and 1:2 and 2:1 protein to ligand concentration ratios before reaction. From the measured TIMES signals of the 4 samples and using (15) and (16) one can find unique solutions for $Q_P(t)$, $Q_L(t)$, $Q_{P-L}(t)$, and $K_d$ at each time point. Since out of the 4 unknowns only $K_d$ is time independent, a histogram for $K_d$ found at each time point can be obtained. This histogram can produce not only the value of $K_d$ but also the quality of the measurement, since a reliable measurement should yield a tight distribution of the $K_d$ value. In other words, in one single set of measurements, $K_d$ can be measured 1000 times over a duration of 1 s at a sampling rate of 1000 s$^{-1}$. FIG. 7b shows the dissociation constant, $K_d$, and FIG. 7c shows the histogram of $K_d$ obtained from the method described above. It was found that the most likely value of dissociation constant for lysozyme and NAG is 12.59 mM. The experiment was repeated three times, and the averaged dissociation constant estimated from TIMES is summarized in Table 4, which also includes previously published value(s) for comparison. The large dissociation constant (i.e., on the order of 10 mM) suggests that the binding between lysozyme and NAG is very weak. The binding can be strengthened significantly by using the trimer of NAG (NAG$_3$), as shown in FIGS. 7(d)-7(f). The histogram shows that the value of the dissociation constant between lysozyme and NAG$_3$ is 39.81 μM (FIG. 7(f)), which is nearly 3 orders of magnitude lower than the value between lysozyme and NAG. The measured value is found to be close to the reported value by other detection methods (see Table 4). It is noted that, besides the complex of lysozyme-NAG or NAG$_3$, the TIMES techniques can be applied to measure the binding constant of different complexes, e.g., trypsin and p-aminobenzamidine, and thermolysin and phosphoramidon, and very precise values can be obtained.

TABLE 4

Comparison of Lysozyme-Ligand Dissociation Constant, Kd, between the TIMES Method and the Previously Published Results Achieved by Other Methods

| ligand | Kd | | | |
|---|---|---|---|---|
| | TIMES | lit. reps | | |
| NAG | 12.59 mM | 16 mM[40] | 24 mM[45] | 7 mM[46] |
| NAG3 | 39.81 μM | 39 μM[44] | 38.3 μM[47] | 19.6 μM[44] |

The TIMES signal waveform shown in FIGS. 7a and 7d demonstrates that the signals produced by protein and protein-ligand appear to be obviously different even though the size, molecular weight, and dipole moment of ligand molecule are orders of magnitude smaller than those of protein. A possible explanation for why a protein bound with a small ligand can produce significant change in the TIMES signal is that ligand binding can alter the folding and/or orientation of protein. Atomistic simulations are disclosed below.

CFD Computations

Figure 8:
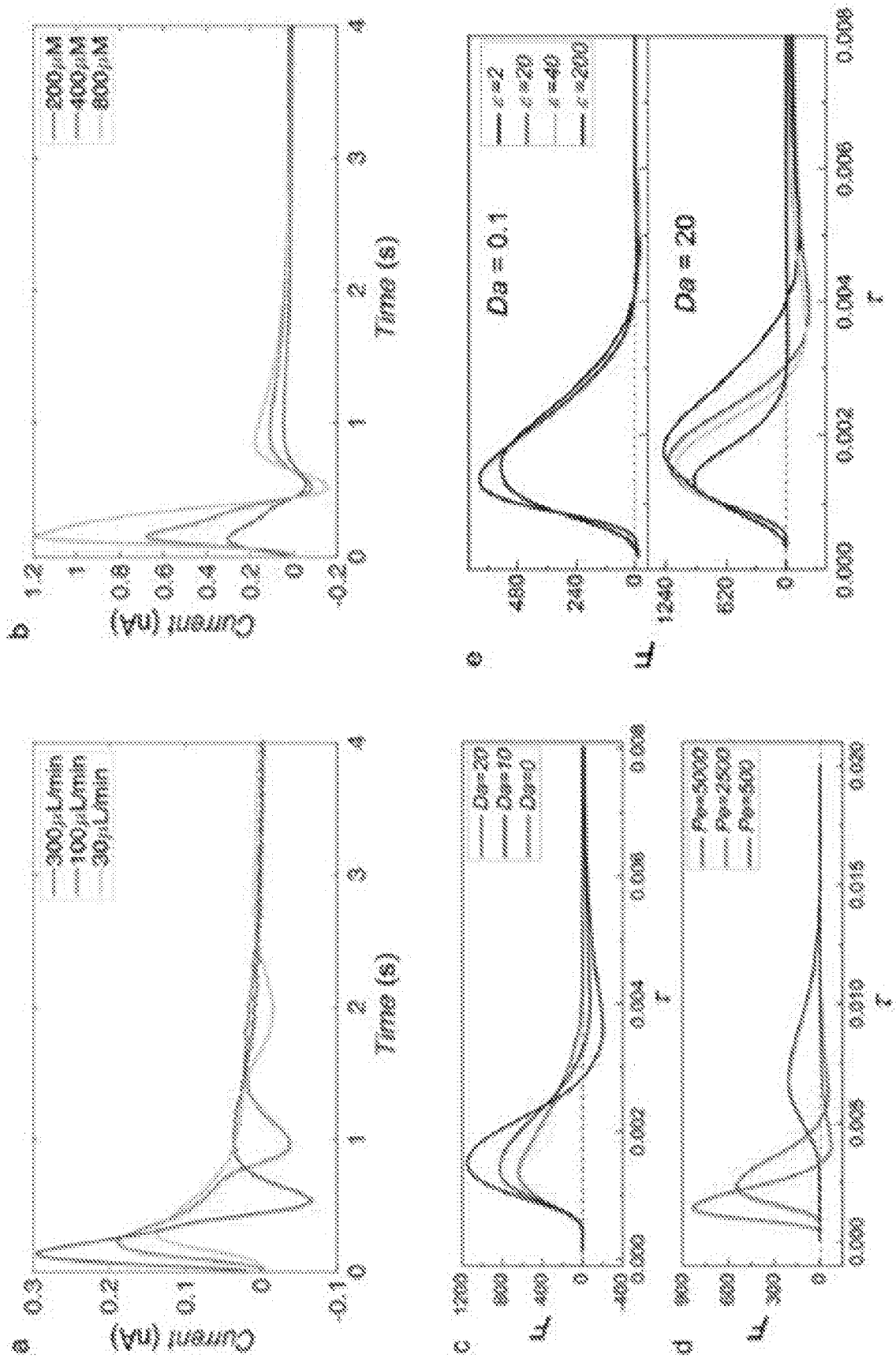
FIGS. 8(a)-8(f) show experimental current measured by TIMES with different lysozyme flow rates (30-300 μL/min) at constant lysozyme concentration of 200 μM (a); different lysozyme concentrations (200-800 μM) at constant flow rate of 300 μL/min (b); the computation of temporal profiles of scaled flux (F) in CFD simulation as a function of dimensionless groups, Da, ε and Pe (corresponding to (c), (d) and (e) labeling on Figures, respectively). The profile (c) was computed at (ε=40 and Pe=5000); the profile (d) was calculated at (ε=40 and Da=10); the profile (e) was at Pe=5000. The dimensionless time (τ) was defined as $$\tau = t\left(\frac{D_{AB}}{h^2}\right).$$

The TIMES electric signal arises from molecular interactions with the electrode surface and is also affected by external hydraulic forces and surface fouling due to protein adsorption. To further investigate the mechanism, both experiments and CFD computations are used. FIG. 8a presents the measured induced currents under different flow rates. By changing the flow rate of lysozyme in the microfluidic channel, the shear stress is changed and so is the driving force to pull the protein away from the electrode. Therefore, the average dwelling time for a protein molecule on the electrode surface is reduced with increased flow rate, which is consistent with the data in FIG. 8a. Different lysozyme concentrations are also examined as shown in FIG. 8b. By flowing different protein concentrations from 200 μM to 800 μM into the microfluidic channel, the signal intensity increases linearly with the concentration as shown in (15) and then saturates as the concentration becomes very high. It is believed that the signal intensity saturation is caused by Coulomb repelling and steric hindrance of molecules near the electrode surface. In other words, the surface adsorption rate $K_+$ in (15) is no longer constant, but decreases with increasing molecular concentration. Finally, all the temporal profiles of the TIMES signal (see FIGS. 8a, and 8b) exhibit a similar characteristic waveform: starting with a fast increase in the signal intensity and followed by a decrease that often displays a negative overshoot before returning to the zero value. Such a general pattern of the waveforms suggests that the waveform follows the protein flux toward the electrode surface. Each time a protein reaches and leaves the electrode, the TIMES signal is produced.

Fluidic dynamic simulation of the mass transfer process inside a microfluidic channel was investigated. CFD computation can be performed with a fluid dynamics model, which consists of diffusion, fully developed laminar flow convection, and surface reactions. Protein-surface interactions are generally significantly stronger than protein-protein interactions, e.g., the lysozyme-Au(111) surface binding free energy (~59 kT) measured from the potential of mean field profile by the umbrella sampling method,[48] compared to lysozyme-lysozyme interaction energy (~0.93 kT) incorporating the hydration and ion effects implicitly through Debye-Hückel theory. Due to the strong surface-protein interactions, it is conceived that the substrate gold surface is covered with a layer of tightly adsorbed proteins and then floppy multilayer adsorption is built up. To simplify the analysis, a Langmuir adsorption model is adopted, in which the effect of surface jamming limit packing is incorporated and only the first-layer adsorption is considered (See (23) in Example 3). Most of the previous studies[50-52] focused on the steady-state adsorption behavior inside a microfluidic channel involve surface adsorption or reactions; whereas the transition state is described herein to interpret the result from TIMES experiments. The equations as well as the initial and boundary conditions are scaled in order to reveal the dimensionless parameters governing the system and to explain the general mechanism. A detailed description of the simulation model and its scaled form are provided in the working examples.

To analyze the effect of the surface reactions, convection, and diffusion on the scaled surface flux (F) in the transition state, dimensionless groups, Damköhler (Da), relative concentration between the bulk and the fully saturated surface (ε), and Péclet (Pe) are introduced, $$F = \frac{dC_A}{dt}\left(\frac{h^2}{D_{AB}C_{A0}}\right) \quad (17)$$

$$Da = K_{ads}C^*_{A(max)}h/D_{AB} \quad (18)$$

$$\varepsilon = \frac{C_{A0}h}{C^*_{A(max)}} \quad (19)$$

$$Pe = Uh/D_{AB} \quad (20)$$

with the initial concentration $C_{A0}$ of protein solution before entering the microchannel, the bulk protein concentration $C_A$ inside the microchannel, protein diffusion coefficient $D_{AB}$, microchannel height h, adsorption rate $K_{ads}$, maximum surface adsorption amount $C_{A^*(max)}$, and the average bulk velocity U. The reduced number $D_a$ represents the ratio of the surface reaction rate and the diffusion rate, and Pe stands for mass transfer rate ratio of convection and molecular diffusion.

FIG. 8c shows that when there is no protein adsorption (i.e., $K_{ads}$=0 or Da=0), no negative overshooting occurs. As Da increases and the value of Pe(=5000) is fixed, both the intensities of flux peak and negative overshooting increase. The results suggest that the surface adsorption can enhance the mass flux toward the surface. When the surface adsorption amount goes beyond the threshold amount, the extra accumulated amount joins the bulk phase, which leads to the signal's negative overshooting. FIG. 8e presents the concentration effects on the scaled surface flux (F) temporal profiles at different Da. The literature shows that Da can vary from the order of ~0.1 to ~10. If the surface fouling reaction is strong (e.g., Da=20), at a constant Pe, the surface flux can be scaled by the concentration. However, for the weak surface fouling reactions (e.g., Da=0.1), the surface flux is not proportional to the concentration increase and the flux reaches its maximum value and declines since the mass transport is limited by surface reactions. FIG. 8d shows the effect of Pe on the scaled flux at a constant ε and Da. Here Pe varies in the range of $10^2$-$10^4$, which is the order of magnitude suggested by previous study. One can observe that when Pe increases (i.e., higher flow speed), the period of transition state shortens, whereas flux intensity and overshooting phenomena become magnified. It indicates that strong convection can enhance mass transfer flux to the surface, due to the large concentration gradient normal to the surface. The results disclosed herein demonstrate that the reduced-unit flux (FIGS. 8d, 8e) from CFD is qualitatively consistent with the experimental results of electric current (FIGS. 8a, 8b). The similarity of their trends illustrates that TIMES electric signal is introduced in the transition state. The CFD simulation may offer good explanations for the negative overshooting of the TIMES signal by attributing this phenomenon to protein adsorption kinetics. The overshooting on protein adsorption kinetics can also be visible in the previous experimental measurements of lysozyme adsorption on the C16 hydrophobic self-assembled surface (SAMs) by using total internal reflectance fluorescence (TIRF).

Atomistic Stimulations

To interpret the surface's electric response at the molecular level, hybrid atomistic simulations are employed. MD simulations are first carried out to simulate the solvation structures of lysozyme and lysozyme-NAG complex. Next, with the solvation structures, the adsorbed lysozyme and lysozyme-NAG complex are predicted by using hybrid MM/PBSA and full-atom MD simulation according to a previously established protocol. Previous studies show that it is computationally expensive to perform full-atom MD simulations to predict protein adsorption in explicit water, and the simulation results are highly dependent on the protein initial orientation, due to the large molecular size and slow rotational motion. Therefore, MM/PBSA can be performed to predict the initial orientation of lysozyme on Au(111) surface at a fixed protein-surface distance by treating protein as a rigid body in an implicit water environment. Then full-atom MD simulations are carried out to relax protein conformation on polarizable Au(111) surfaces.

Figure 9:
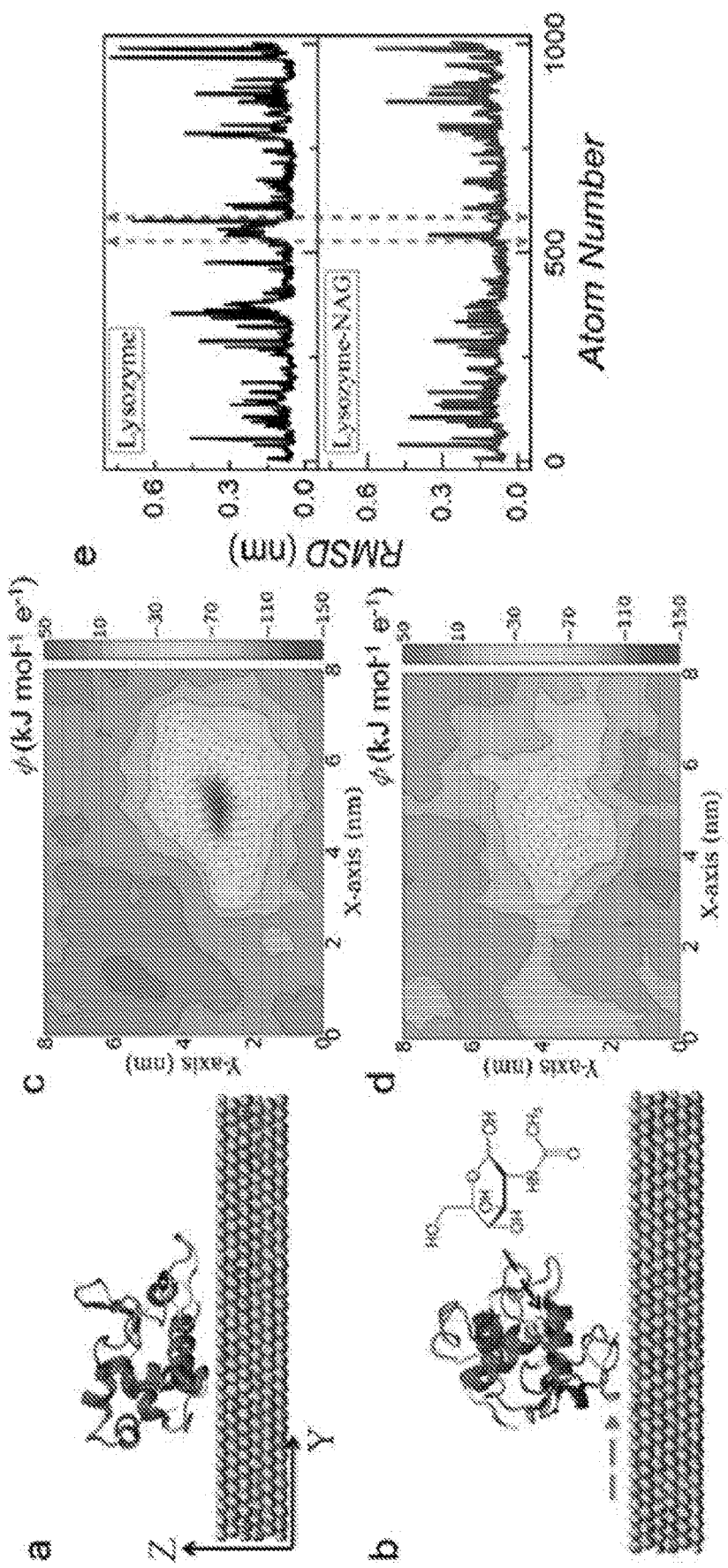
FIGS. 9(a)-9(e) show examples of snapshots of lysozyme before (a) and after (b) binding with NAG on Au (111) surface from atomistic simulations for 20 ns, their corresponding contours (c, d) of induced gold surface electric potential φ on the X-Y plane above the surface of 0.3 nm by taking average with the configurations of the last 2 ns, and the comparison of RMSD of simulated solution structures of pure lysozyme and lysozyme of the complex binding with NAG ligand (e). RMSD profiles for pure lysozyme and lysozyme of the lysozyme-NAG complex solution structures. In RMSD computation, the first conformation of the sampled trajectories was used as a reference. The area around atom #514-587 is indicated with arrows on the snapshots (b) and RMSD curves (e) respectively. The atom number is only for heavy backbone atoms. For the purpose of clarity, water and ions are excluded from the snapshots (a, b). The induced surface electric potential was computed by fixing lysozyme (or lysozyme-NAG complex) configuration to relax the system for 2 ns. The last 1 ns data including total 200 configurations was used to take the average of φ.
Figure 10:
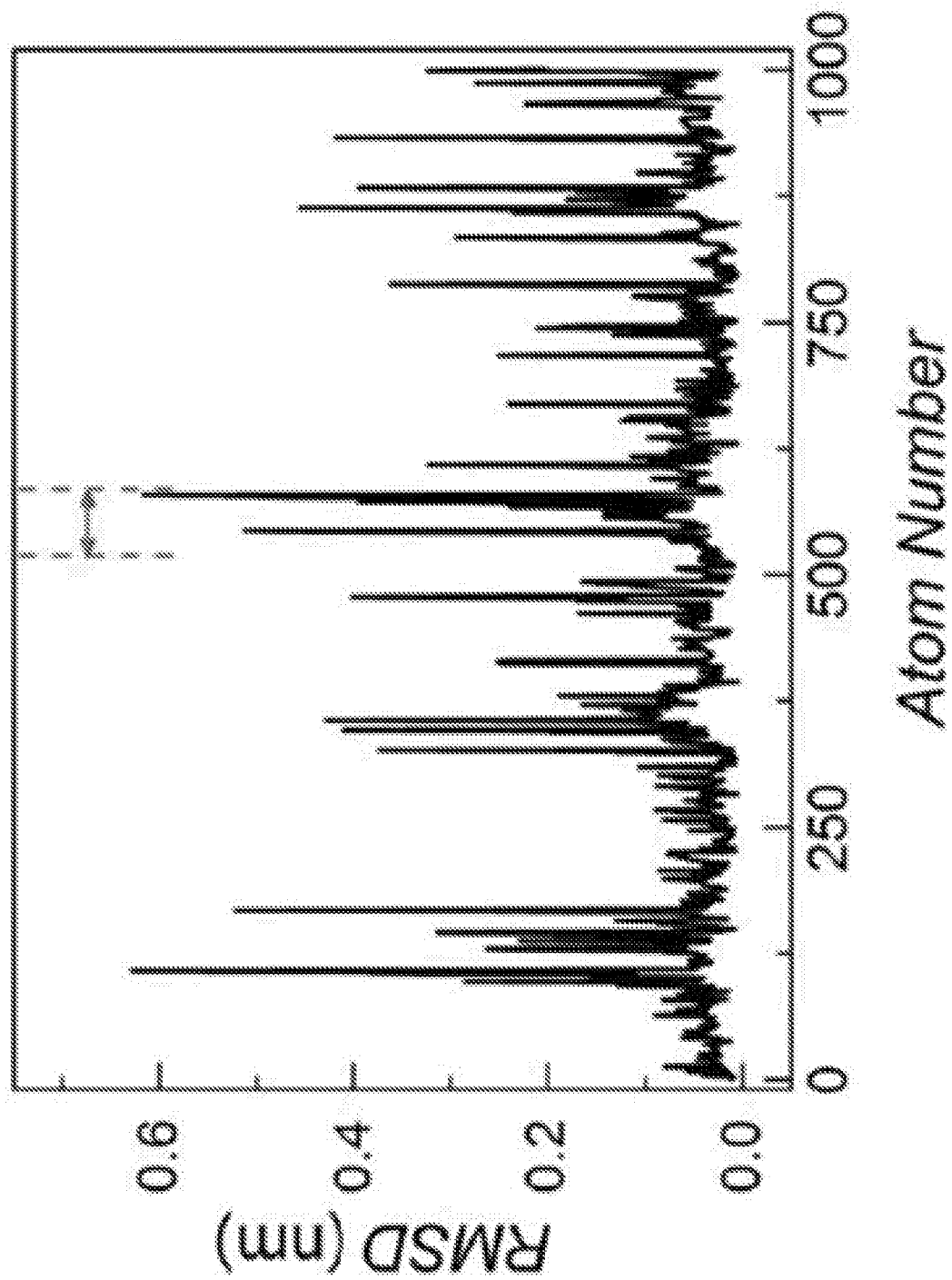
FIG. 10 shows structural variance characterized by RMSD between pure lysozyme (pdb code: 1AKI) and lysozyme in lysozyme-NAG complex (pdb code: 3TXJ). The structures were taken from protein data bank. Protein of the complex was taken as a reference. The region (atom#514-587) is indicated with arrows. The atom number is only for heavy backbond atoms.

MM/PBSA computations show that, before binding with ligand NAG, the lysozyme molecule most likely "lies down" with residues (Ile78-Asn93) contacting the gold surface, whereas the lysozyme-NAG complex most possibly "stands up" with residues (Asn65-Asn74) close to the Au(111) substrate surface. After 25 ns further relaxation with MD simulations, both protein and protein-ligand complex undergo slight conformational changes. FIGS. 9a and 9b compare the final different conformations of pure protein and the complex. Consequently, their dipole moment directions are very different leading to distinct gold surface polarization. For a pure lysozyme, the angle between the dipole moment vector and positive Z-axis normal to the surface is (90.36±4.98)°, while for NAG-lysozyme, the angle is (27.86±8.10)°. To characterize the gold surface polarization, the X-Y plane above the gold substrate above the top of the gold surface (8.075×7.992 nm²) is divided into 17×17 grids. At each grid point of the position $\vec{r}$, the electric potential φ (kJ mol$^{-1}$e$^{-1}$) of the gold surface's image charges is calculated by summing up the Coulombic interactions over all surface atoms N, $$\phi = f\sum_{i=1}^{N}\frac{q_i}{|\vec{r}-\vec{r}_i|} \quad (21)$$

with electric conversion factor f=138.935 kJ mol$^{-1}$ nm e$^{-2}$ and the surface atom i position $\vec{r}_i$. The electric potential contour shows the overall effect of protein's charge distribution as well as all other contributions from solvent environment, i.e., hydration water and ions. As shown in FIG. 9c, 9d, different contours of induced electric potential resulting from gold substrate surface image charges are detected for the adsorbed pure lysozyme and lysozyme-NAG complex. To further investigate the reason for different lysozyme adsorption orientations before and after ligand-binding, root-mean-square displacement (RMSD) of protein's heavy backbone excluding hydrogen atoms (see FIG. 9e) is introduced to quantify protein structural stability. By using MD simulation trajectories of both pure lysozyme and lysozyme-NAG complex, RMSD is computed after an optimal overlap, where each instantaneous structure is translated and rotated to superimpose the reference structure. From RMSD profile of pure lysozyme and NAG-lysozyme complex, it is shown that compared to the lysozyme solvation structure, lysozyme bound with the NAG ligand displays smaller structural fluctuations, particularly around the area (atom #514-587) corresponding to the adsorption region (Asn65-Asn74) for the complex. For further verification, experimental structure data from the Protein Data Bank is examined. RMSD is computed to compare structures of both pure protein and protein of a complex. The same large variance is also detected at that particular area, i.e., Asn65-Asn74 (see FIG. 10). Previous studies showed that a gold surface has a large surface energy. Protein's slight structural rearrangement can affect protein adsorption orientation due to the strong dehydration free energy of the gold surface. For a lysozyme molecule, sulfur atoms are not exposed to the solvent environment. Therefore, the possibility of thio (Au—S) interaction between protein and gold surface can be excluded, particularly at the earlier stage when a protein molecule reaches the gold surface. Given the aforementioned analysis, it can be concluded that the binding of NAG results in the variance in lysozyme structural stability and hence affects protein dipole moment direction, which induces different electric responses as the detected TIMES signal.

As disclosed herein, the technique of Transient Induced Molecular Electronic Spectroscopy (TIMES) can detect protein-ligand binding in aqueous phase without fluorescent labeling or surface immobilization of molecules. The TIMES technique allows the study of undisturbed interactions between protein and ligand. The method is based on experiment and physical computations, and is established partly on the principle that protein-ligand binding can result in detectable changes in protein's charge distribution and dipole moment even though the protein-ligand complex has nearly the same molecular weight and chemical makeup as the protein itself. The physics of the signals are mathematically formulated to make the TIMES technique not only a qualitative tool but also a quantitative method to analyze the protein interactions. TIMES method can produce, for example, measurements of dissociation constant for protein-ligand binding and shear-stress dependent adsorption time for protein and protein/ligand complex. The TIMES method can also be used to study protein folding, binding kinetics, protein-protein interaction, protein-aptamer interaction, and other properties important for drug discovery and protein chemistry.

As described herein and demonstrated in the working examples, the TIMES method can accurately measure the dissociation constant for lysome-NAG and lysozyme-NAG$_3$ interactions and demonstrated that, compared to monomer NAG, trimer NAG$_3$ can enhance the binding with lysozyme by nearly 1000 times. The theory presented herein was further examined experimentally with different concentrations and flow rates of protein in a microfluidic channel as well as theoretically by performing CFD and atomistic simulations.

The CFD simulations suggest that attractive protein-electrode force and repulsive shear force in a microfluidic channel determine the surface flux of protein, which gives the general waveform of the TIMES signal characterized by a positive peak followed by a negative overshoot before returning to the baseline. With the induced electrical signal from proteins dwelling on the electrode surface, the effects of protein and ligand concentration and hydraulic shear stress on protein-ligand binding and proteins' kinetic transport at the water-surface interface inside a microfluidic channel were investigated. The efficient hybrid MM/PBSA calculations and MD simulations predict the most probable adsorption orientations of protein and protein-ligand complex and the subsequent surface polarization. The results indicate that protein configuration change due to ligand binding contributes to the TIMES signal and enables the method to detect protein-ligand interactions and find the reaction dissociation constant. Although protein-ligand interactions are used as examples, the technique and general principle of TIMES can be easily extended to study interactions of different kinds of molecules as an effective tool to characterize biomolecular reactions in conditions closest to their native environments. Such examples include interactions between proteins and nucleic acids, proteins and aptamers, aptamers and small (drug) molecules, etc. Additionally, disclosed herein is the TIMES method used for characterization of protein-ligand interactions with a single binding site. More complicated systems involving multiple-ligand binding can be developed and used based on this disclosure.

In some embodiments, the detection of protein-ligand binding may thus be used laboratory testing, drug discover, understanding and calibrating reactions and other research and development purposes. Using the amount of protein-ligand binding and by calculating rate at which the binding occurs, e.g., drug delivery and dosage calculations may be performed.

WORKING EXAMPLES

The following examples illustrate various embodiments of the technology disclosed in this document. By no means the following examples limit the scope of the invention in any way.

Example 1 TIMES Experiment Setup

Device Fabrication:

The TIMES system consists of a microfluidic channel to allow the biomaterials to flow through, a pair of gold electrodes on the floor of the microfluidic channel as the sensing electrode and ground electrode, two inlets to inject molecules of interest and buffer respectively, and a transimpedance amplifier with its input connected to the gold sensing electrode. The device was fabricated on a 1 mm thick glass slide (VWR). Before fabrication, the glass slide was cleaned in acetone, methanol, and isopropyl alcohol (IPA) for 5 minutes in each chemical sequentially with sonication, and blow-dried by nitrogen gas. The glass slide was first lithographically patterned by NR9-1500PY photoresist (Futurrex, USA). After deposition of 100 nm titanium (Ti) and 200 nm gold (Au) films on the glass slide using a sputtering system (Denton Discovery 18, Denton Vacuum, LLC), lift-off process with low power sonication was employed to remove the photoresist to form the Ti/Au patterns. Each Ti/Au sensing area was 1×1 mm$^2$ with an extended area outside of the channel to allow connection to the external circuits via soldered wires. The microfluidic channel was fabricated using soft lithography process. The mold was fabricated on a 4 inches Si wafer. After the standard wafer cleaning process, a layer of 30 μm thick SU8-2050 (Microchem) photoresist was spun on the silicon wafer and patterned photolithographically to form the SU8 mold. Uncured polydimethylsiloxane (PDMS, Sylgard 184, Dow Corning, Mich.) was poured onto the SU8 mold and cured in a 65° C. oven. Two parts of PDMS (base: curing agent=10:1) were well mixed and degased in a vacuum chamber, and were poured onto the SU-8 mold and cured at 65° C. for 4 hours. After curing, PDMS was separated from the SU-8 mold and holes were punched on the PDMS to form inlets and outlets. Finally, after UV ozone treatment the PDMS part and the Ti/Au patterned glass slide were aligned under microscope, and baked on 120° C. hotplate for half an hour to ensure bonding, which produced the device in FIG. 1.

Experiment Setup:

The two inlets of microfluidic channel were connected to two syringes (BD plastic) that contained buffer and buffer with dissolved protein/ligand. The flow rates of the syringes were controlled by programmable syringe pumps (Pump 11 elite, Harvard Apparatus). One gold sensing area within the microfluidic channel was connected electrically to the input of a low noise transimpedance amplifier (SR570, Stanford Research System, Inc.), and the other gold pad within the microfluidic channel was connected to the ground of the circuit. The transimpedance of the amplifier was set at 100 MΩ, and the voltage output of the amplifier was digitized by a DAQ board (National Instrument USB-6251). The data were recorded and filtered using LabVIEW Signal Express, at a sampling rate of 1 kHz. The primary sources of noise are interference from the environment and thermal noise of transimpedance amplifier. Using an electro-magnetic shielded chamber, an improved amplifier with lower thermal noise, and digital filters (Labview), the signal-to-noise ratio can be improved to allow the measurement of reactions with very low (e.g., pM) dissociation constant.

All the components in the setup, including the stainless steel needles connecting the syringes and the inlets of the microfluidic channels were grounded electronically. Before the experiment, the microfluidic channel was flushed and filled with buffer injected from both inlets (FIG. 1b, i). Then one of the inlets was replaced with protein (or other molecules of interest) laden buffer to fill up the channel, as shown in FIG. 1b, ii. Then the syringe pump that drove the protein was stopped and the other syringe pump driving the buffer was turned on to wash the channel. The above procedure completed the conditioning of the system before test, leaving a liquid interface between protein and buffer solution near the input of the channel, as shown in FIG. 1b, iii. To start the experiment, the flow of the buffer was stopped and the protein laden solution flowed through the microfluidic channel (FIG. 1b, iv). The TIMES signal was generated as shown in FIGS. 1(c)-1(e).

Data Analysis:

After testing protein, ligand, and different ratios of protein and ligand mixture, signals were processed by applying the physical model discussed below to attain such information as induced charge response q(t), protein (or protein/ligand complex) adsorption time $\tau_s$, and dissociation constant $K_D$. The physical model was implemented in Matlab.

Unless mentioned otherwise, 5 mM Tris-HCl buffer was used for all the experiments reported in this disclosure, including the control experiments described in the following. To show that protein flux from a concentration gradient contributes to the TIMES signal, a reverse concentration gradient for trypsin was created by first filling the channel with trypsin and then flowing buffer into the channel to drive the trypsin away from the electrode. By reversing the protein concentration gradient, the polarity of the TIMES signal was also reversed (FIG. 4a).

Negative control experiment was conducted by introducing Tris-HCl buffer into a Tris-HCl buffer filled channel. The absence of any detectable signal (FIG. 4b) suggests that no signal was produced by artifact such as temperature gradient or flow-induced shear stress.

A more complete list of dipole moments of protein can be found in Protein Dipole Moments Server (http://dipole.weizmann.ac.il/) and Pitt Quantum Repository Molecular Database (https://pqr.pitt.edu/).

Example 2 Biomolecule Test on TIMES

Before the test, the microfluidic channel was first filled with buffer from inlet. Chosen amounts of protein and ligand were dissolved in buffer solution before the test. For samples that contained both protein and ligand molecules, the samples were set aside for 3 h before the test to ensure that the reaction had reached the equilibrium state. All the measurements were conducted at room temperature, and each test was repeated three times to confirm repeatability. After each test, the device was washed with buffer to remove any molecule residues in the microfluidic channel or on the electrode surface. The protein and ligand binding experiments were performed in 1×PBS buffer at pH=7.4. The data obtained after the amplifier and ADC were low pass filtered digitally in Matlab to remove noise, and the dissociation constant $K_d$ was calculated and plotted with Matlab. TIMES dissociation constant ($K_d$) estimation is detailed below. The protein experiment under different flow rates and concentrations was performed in 50 mM Tris-HCl buffer at pH=7.4.

The measured signal of TIMES system can be represented as $$i(t) \sim A \sum_i n_{o,i} K_{+,i} \gamma_i q_i(t - t_{oi}) \text{ where } t_{oi} = \frac{4L^2}{D_i} \quad (i)$$

In the case of first-order reaction:

Ligand + Protein ↔ PLcomplex $$K_d = \frac{n_L n_P}{n_C} \quad (ii)$$

$$i(t) \sim A[n_{o,P} K_{+,P} \gamma_P q_P(t) + n_{o,L} K_{+,L} \gamma_L q_L(t) + n_{o,C} K_{+,C} \gamma_C q_C(t)] \quad (iii)$$

Define: $G_P(t)=K_{+,P}\gamma_P q_P(t)$  $G_L(t)=K_{d,L}\gamma_L q_L(t)$ 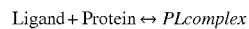
$G_C(t)=_{+,C}\gamma_C q_C(t)$ Before reaction, the initial protein and ligand concentration are assumed to be x and y, respectively. After the equilibrium is reached, $$n_{o,p} = x - z, n_{o,L} = y - z, n_{o,c} = z \quad (iv)$$

$$K_d = \frac{(x-z)(y-z)}{z}$$

Solving z from (iv), $$n_{o,c} = z = \frac{(x+y+K_d) - \sqrt{(x+y+K_d)^2 - 4xy}}{2} \quad \text{(v1)}$$

$$n_{o,p} = x - z = \frac{(x-y-K_d) + \sqrt{(x+y+K_d)^2 - 4xy}}{2} \quad \text{(v2)}$$

$$n_{o,L} = y - z = \frac{(y-x-K_d) + \sqrt{(x+y+K_d)^2 - 4xy}}{2} \quad \text{(v3)}$$

Substituting (v) into (iii)

$$i(t) \sim A\{[(x-y-K_d) + \sqrt{(x+y+K_d)^2 - 4xy}]G_P(t) + [(y-x-K_d) + \sqrt{(x+y+K_d)^2 - 4xy}]G_L(t) + [(x+y+K_d) - \sqrt{(x+y+K_d)^2 - 4xy}]G_c(t)\} \quad \text{(vi)}$$

To obtain $K_d$, the following special cases for x and y can be used: By adding the same amount of protein and ligand to the buffer (i.e. x=y)

$$i(t)|_{y=x\neq 0} \sim A\{[(-K_d) + \sqrt{K_d^2 + 4xK_d}]G_P(t) + [(-K_d) + \sqrt{K_d^2 + 4xK_d}]G_L(t) + [(2x+K_d) - \sqrt{K_d^2 + 4xK_d}]G_c(t)\} \quad \text{(vii1)}$$

By adding a fixed amount of protein and twice the amount of ligand to the buffer (i.e. y=2x):

$$i(t)|_{y=2x\neq 0} \sim A\{[(-x-K_d) + \sqrt{(3x+K_d)^2 - x8^2}]G_P(t) + [(x-K_d) + \sqrt{(3x+K_d)^2 - x8^2}]G_L(t) + [(3x+K_d) - \sqrt{(3x+K_d)^2 - x8^2}]G_c(t)\} \quad \text{(vii2)}$$

By adding only protein to the buffer without ligand (i.e. y=0):

$$i(t)|_{y=0} \sim AxG_P(t) \quad \text{(viii1)}$$

By adding only ligand to the buffer without protein (i.e. x=0):

$$i(t)|_{x=0} \sim AyG_L(t) \quad \text{(viii2)}$$

As a result, the dissociation constant Kd can be obtained by solving Equations (vii), (viii). Also, the "temporal response" of protein, ligand, and protein-ligand complex, represented by $G_P(t)$, $G_L(t)$, and $G_C(t)$, respectively, can be obtained.

Example 3 CFD Computation

The transport of lysozyme solution inside a microchannel was modeled with the mass transfer equation (22), which included convection and diffusion, coupled with surface adsorption (23), $$\frac{\partial C_A}{\partial t} = \nabla \cdot (D_{AB} \nabla C_A) - V \cdot \nabla C_A \quad \text{(22)}$$

$$\frac{dC_A^*}{dt} = K_{ads} C_{AS} (C_{A(max)}^* - C_A^*) - K_{des} C_A^* \quad \text{(23)}$$

with lysozyme bulk concentration $C_A$, bulk solution concentration near the surface $C_{AS}$, surface adsorption concentration $C_A^*$, and maximum surface adsorption amount $C_{A(max)}^*$. Due to large protein-surface binding free energy, $K_d u$ was ignored in the computation to simplify the analysis. A fully developed laminar velocity profile was adopted. The microfluidic channel was initially filled with pure water before being flushed with protein solution of concentration $C_{A0}$. The governing equations, initial and boundary conditions in dimensional and scaled forms are shown below. COMSOL multiphysics software (Version 5.1, COMSOL Inc. USA) was used to solve the partial differential equations.

Figure 12:
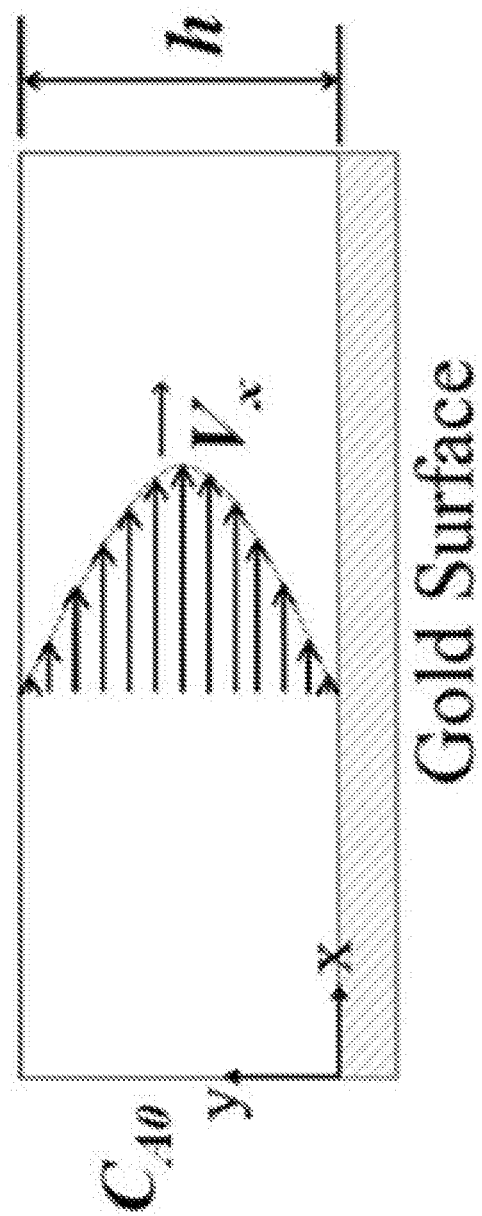
FIG. 12 shows schematics of a microfluidic channel. Protein solution of concentration $C_{A0}$ is injected into a microchannel of the height, h.

The mass transfer equation, which consists of convection and diffusion, coupled with the surface adsorption are simplified in 2-dimension as shown in FIG. 12:

$$\frac{dC_A}{dt} + \frac{V_x dC_A}{dx} = \frac{D_{AB} d^2 C_A}{dy^2} \quad \text{(ix)}$$

Here, $C_A$ is protein concentration, $D_{AB}$ is protein diffusivity and the fully developed laminar velocity profile is $V_x = 60_h^L(1 \ldots {_h}^Z)$ and U is the averaged velocity. The adsorption and desorption from biosensor surface are described by Langmuir adsorption model:

$$\frac{dC_A^*}{dt} = K_{Ads} C_{AS} (C_{A(max.)}^* - C_A^*) - K_{Des} C_A^* \quad \text{(x)}$$

Where $C_A^*$ is surface concentration, $K_{Ads}$ and $K_{Des}$ are adsorption and desorption rate constants, $C_{A(max)}^*$ is maximum surface concentration and $C_{AS} = C_A(y=0)$.

The BCs and ICs are the following:

BC. 1: at $x = 0$, $C_A = C_{A0}$      (xi)

BC. 2: at $y = 0$ and $x > 0$,      (xii)

$$D_{AB} \frac{dC_A}{dy} = \frac{dC_A^*}{dt} = K_{Ads} C_{AS} (C_{A(max.)}^* - C_A^*) - K_{Des} C_A^*$$

BC. 3: at $y = h$ and $x > 0$, $\frac{dC_A}{dy} = 0$      (xiii)

IC. 1: at $t = 0$ and $x > 0$, $C_A = 0$      (xiv)

IC. 2: at $t = 0$ and $x > 0$, $C_A^* = 0$      (xv)

The dimensionless parameters listed in Table 5 are introduced to scale the equations (ix)-(xv):

TABLE 5

| Definitions of Dimensionless Groups | |
| --- | --- |
| Dimensionless Parameter | Definition |
| $\theta_A = \dfrac{C_A}{C_{A0}}$ | Concentration |
| $\theta_A^* = \dfrac{C_A^*}{C_{A(max.)}^*}$ | Surface concentration |
| $\zeta = \dfrac{x}{h}$ | Channel Length |
| $\eta = \dfrac{y}{h}$ | Channel Height |
| $\tau = \dfrac{D_{AB} t}{h^2}$ | Diffusion time |
| $Pe = \dfrac{Uh}{D_{AB}}$ | Péclet number |

TABLE 5-continued

Definitions of Dimensionless Groups

| Dimensionless Parameter | Definition |
|---|---|
| $Da = \dfrac{K_{Ads} C^*_{A(max)} h}{D_{AB}}$ | Damköhler number |
| $K_D = \dfrac{K_{Des}}{C_{A0} K_{Ads}}$ | Equilibrium constant |
| $\varepsilon = \dfrac{C_{A0} h}{C^*_{A(max.)}}$ | Relative concentration |

The scaled form of governing equation is $$\frac{d\theta_A}{d\tau} + 6\eta(1-\eta) Pe \frac{d\theta_A}{d\zeta} = \frac{d^2\theta_A}{d\eta^2} \quad \text{(xvi)}$$

The scaled form of the surface reaction is $$\frac{d\theta_A^*}{d\tau} = \varepsilon Da[\theta_{AS} \cdot (1-\theta_A^*) - K_D \theta_A^*] \quad \text{(xvii)}$$

The scaled form of the BCs and ICs are

BC. 1: at $\zeta = 0$, $\theta_A = 1$ \quad (xviii)

BC. 2: at $\eta = 0$, $\dfrac{d\theta_A}{d\eta} = \dfrac{1}{\varepsilon}\dfrac{d\theta_A^*}{d\tau} = Da[\theta_{AS} \cdot (1-\theta_A^*) - K_D \theta_A^*]$ \quad (xix)

BC. 3: at $\eta = 1$, $\dfrac{d\theta_A}{d\eta} = 0$ \quad (xx)

IC. 1: at $\tau = 0$, $\theta_A = 0$ \quad (xxi)

IC. 2: at $\tau = 0$, $\theta_A^* = 0$ \quad (xxii)

Example 4 Atomistic Simulations

MD simulations were performed with Gromacs software package (version 4.6.5)[63] in NVT ensemble by using Charmm36 force field for protein and NAG molecules, and tip3p water model. Lysozyme crystal structure (pdb code: 3TXJ) was obtained from the Protein Data Bank and was with a net charge of +8e at pH 7 (see details below). The system was neutralized by adding Cl⁻ ions. In addition, 40 pairs of Na⁺ and Cl⁻ were added into the system to keep the ion concentration equal to 120 mM. To obtain solvation structures, pure lysozyme and lysozyme-NAG complex were first equilibrated in water environment for 50 ns. Detailed discussion about MD simulation is shown below.

Of the amino acids, arginine (Arg) and lysine (Lys) were protonated, glutamate (Glu) and aspartate (Asp) were deprotonated, and histidine (His) was treated neutral, resulting in a net charge of +8e at pH 7. The N and C termini remained uncapped. Time integration was performed with leap-frog algorithm using a time step of 1 fs. Berendsen thermostat at 298 K was used. The particle mesh Ewald summation was adopted to calculate long-range electrostatic interactions with a cut-off distance of 1.2 nm for the separation of the direct and reciprocal spaces. A spherical cut-off at 1.2 nm was imposed on Lennard-Jones interactions. The long-range dispersion effect was also calibrated.

A two-step procedure was adopted to predict protein adsorption and consequent surface polarization. First, hybrid molecular mechanics/Poisson-Boltzmann surface area (MM/PBSA) computations were performed to predict the protein initial orientation on Au (111) surface based on protein binding free energy, which consisted of protein-surface interactions and hydration or dehydration free energy, according to a previously established protocol to serve as an initial value for the following MD simulations. In MM/PBSA, the solvated protein and protein-NAG complex were treated as rigid bodies respectively, and were rotated around their center of mass on Au (111) surface (8.075×7.992 nm²) while fixing protein-surface minimum distances (i.e., 0.3 nm) to search for the most energetically favorable orientations. To simplify the computation in MM/PBSA, the nonpolarizable Au surface parameters were used for the Au-protein and Au-water interactions. The protein-surface distance was also changed to 0.26 nm, which was closer to the surface, and the same most top-ranking orientations for both pure protein and complex were identified from MM/PBSA. The surface tension of Au (111) ($\gamma=1.41$ J/m²) was adopted from the literature report in MM/PBSA computations. Second, a full relaxation of the initial adsorbed lysozyme and lysozyme-NAG configurations was performed with full-atom MD simulations for 20 ns with polarizable force field parameters of Au (111) surfaces, which was developed by Walsh et al. and accounts for the interactions between peptides or protein and the induced surface image charges by introducing dummy atoms to form rigid-rod dipoles free to rotate around atomic sites. Surface atoms were aligned with periodic boundary image atoms in accordance with the gold crystal lattice to mimic a large surface without boundary effects. Two repulsive walls were built on the top and bottom layers of the z-direction to confine solvent molecules. At the top of the gold surface, a water box of 7.6 nm height was built.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

We claim:

1. A method of detecting a molecule in a solution comprising:
   conditioning a microfluidic channel;
   allowing a solution containing the molecule to flow through a first inlet connected to the microfluidic channel;
   receiving a signal generated by the molecule in contact with an electrode in the microfluidic channel;
   performing an analog-to-digital conversion of the signal to generate a digitized signal; and
   processing the digitized signal by a processor to obtain a transient induced molecular electronic spectroscopy (TIMES) dissociation constant of the molecule.

2. The method of claim 1, wherein conditioning the microfluidic channel comprises:
   injecting a first buffer solution through the first inlet and a second inlet to flush the microfluidic channel;
   injecting the solution containing the molecule through the first inlet;
   stopping the injection of the first inlet;
   injecting a second buffer solution through the second inlet to wash the microfluidic channel,
   such that a liquid interface between the solution containing the molecule and the second buffer solution forms near the input of the microfluidic channel.

3. The method of claim 1, wherein the molecule is a protein, a ligand, or a protein-ligand complex.

4. A method of detecting the binding of molecules from different solutions, comprising:
   (a) detecting a first molecule of a first solution according to:
      conditioning a microfluidic channel,
      allowing the first solution containing the first molecule to flow through a first inlet connected to the microfluidic channel,
      receiving a signal generated by the first molecule in contact with an electrode in the microfluidic channel,
      performing an analog-to-digital conversion of the signal to generate a digitized signal associated with the first molecule, and
      processing the digitized signal associated with the first molecule by a processor to obtain a first transient induced molecular electronic spectroscopy (TIMES) dissociation constant of the first molecule;
   (b) detecting a second molecule of a second solution according to:
      conditioning the microfluidic channel,
      allowing the second solution containing the second molecule to flow through a second inlet or the first inlet connected to the microfluidic channel,
      receiving a signal generated by the second molecule in contact with the electrode in the microfluidic channel,
      performing an analog-to-digital conversion of the signal to generate a digitized signal associated with the second molecule, and
      processing the digitized signal associated with the second molecule by the processor to obtain a second TIMES dissociation constant of the second molecule;
   (c) mixing the first molecule and the second molecule in a single solution such that a complex is formed between the two molecules;
   (d) detecting the complex of the first molecule and the second molecule of the single solution according to:
      conditioning the microfluidic channel,
      allowing the single solution containing the complex to flow through a third inlet, the second inlet, or the first inlet connected to the microfluidic channel,
      receiving a signal generated by the complex in contact with the electrode in the microfluidic channel,
      performing an analog-to-digital conversion of the signal to generate a digitized signal associated with the complex, and
      processing the digitized signal associated with the complex by the processor to obtain a third TIMES dissociation constant of the complex; and
   (e) comparing the TIMES dissociation constants associated with the first molecule, associated with the second molecule, and associated with the complex of the first molecule and the second molecule to determine the binding of the first molecule and the second molecule.

5. The method of claim 4, wherein the first molecule and the second molecule are a protein and a ligand, respectively.

6. The method of claim 4, wherein different ratios of the first molecule and the second molecule are mixed to form the complex.

7. The method of claim 4, wherein the difference in a molecular weight and chemical composition between the first molecule and the complex of the first molecule and the second molecule is less than 1%.

8. The method of claim 4, wherein the difference in a molecular weight and chemical composition between the second molecule and the complex of the first molecule and the second molecule is less than 1%.

9. The method of claim 4, wherein determination of the binding of the first molecule and the second molecule is performed without any modification, labeling, or immobilization of the first molecule or the second molecule.

* * * * *